(12) United States Patent
Sumida

(10) Patent No.: US 7,419,800 B2
(45) Date of Patent: Sep. 2, 2008

(54) ESTROGEN RECEPTOR GENES

(75) Inventor: Kayo Sumida, Neyagawa (JP)

(73) Assignee: Sumitomo Chemical Company Limited, Osaka (JP)

( * ) Notice: Subject to any disclaimer, the term of this patent is extended or adjusted under 35 U.S.C. 154(b) by 712 days.

(21) Appl. No.: 10/451,768

(22) PCT Filed: Nov. 15, 2001

(86) PCT No.: PCT/JP01/09995

§ 371 (c)(1),
(2), (4) Date: Jun. 24, 2003

(87) PCT Pub. No.: WO02/052010

PCT Pub. Date: Jul. 4, 2002

(65) Prior Publication Data

US 2004/0115765 A1    Jun. 17, 2004

(30) Foreign Application Priority Data

Dec. 25, 2000   (JP) .............................. 2000-392262

(51) Int. Cl.
*C12N 15/11* (2006.01)
*C12N 15/63* (2006.01)
*C12N 5/10* (2006.01)

(52) U.S. Cl. .................... 435/69.1; 435/320.1; 435/325; 536/23.5

(58) Field of Classification Search ........................ None
See application file for complete search history.

(56) References Cited

FOREIGN PATENT DOCUMENTS

JP    2000-201688 A   7/2000
WO    WO 99/11760 A1  3/1999

OTHER PUBLICATIONS

Krust, et al., "The chicken oestrogen receptor sequence: homology with v-erbA and the human oestrogen and glucocorticoid receptors", *The EMBO Journal*, vol. 5, No. 5, pp. 891-897 (1986).

Jacobs, et al., "Zebra Finch Estrogen Receptor cDNA: Cloning and mRNA Expression", *J. Steroid Biochem. Molec. Biol.*, vol. 59, No. 2, pp. 135-145 (1996).

Bökenkamp, et al., "The C-terminal half of the porcine estradiol receptor contains no post-translational modification: determination of the primary structure", *Molecular and Cellular Endocrinology*, vol. 104, pp. 163-172 (1994).

Vidal, et al., "Survey and summary: Yeast forward and reverse 'n'-hybrid systems", *Nucleic Acids Research*, vol. 27, No. 4, pp. 919 to 929 (1999).

Young, et al., "Reptilian Sex Steroid Receptors: Amplification, Sequence and Expression Analysis", *J. Steroid Biochel. Molec. Biol.*, vol. 55, No. 2, pp. 261-269 (1995).

Matthews, et al., "Differential Binding Affinities of PCBs, HO-PCBs, and Aroclors with Recombinant Human, Rainbow Trout (*Onchorhynkiss mykiss*), and Green Anole (*Anolis carolinensis*) Estrogen Receptors, Using a Semi-High Throughput Competitive Binding Assay", *Toxicological Sciences*, vol. 53, pp. 326-339 (2000).

*Primary Examiner*—Michael Pak
(74) *Attorney, Agent, or Firm*—Panitch Schwarze Belisario & Nadel LLP

(57) ABSTRACT

The present invention relates to an estrogen receptor gene, characterized by comprising a nucleotide sequence coding for any one of the following amino acid sequences:

(a) the amino acid sequence of SEQ ID NO:1,
(b) an amino acid sequence of a protein having an estrogen receptor activity, said amino acid sequence has at least 85% sequence identity with the amino acid sequence of SEQ ID NO:1,
(c) an amino acid sequence encoded by the nucleotide sequence of SEQ ID NO:2, and
(d) an amino acid sequence of a protein having an estrogen receptor activity, said amino acid sequence is encoded by a nucleotide sequence having at least 85% sequence identity with a DNA having the nucleotide sequence of SEQ ID NO:2, and the like. The estrogen receptor gene and the like can be applied to assay systems for evaluating the ability of chemical substances to regulate the estrogen receptor activity.

16 Claims, 3 Drawing Sheets

ESTROGEN RECEPTOR GENES

CROSS-REFERENCE TO RELATED APPLICATION

This application is a Section 371 of International Application No. PCT/JP01/09995, filed Nov. 15, 2001, the disclosure of which is incorporated herein by reference.

TECHNICAL FIELD

The present invention relates to estrogen receptor genes and the utilization thereof.

BACKGROUND ART

In recent years, some environmental chemical substances have been reported to have estrogen-like activity, and for example, feminization of wildlife has been reported on some types of chemical substances (T. Colborn, D. Dumanoski and J. P. Myers, Our Stolen Future, 1996, Dutton, N.Y.). The activity of such chemical substances leads to a disturbance of hormone balance in various organisms including human and can cause disorders or diseases. Thus, the measurement of the estrogen-like activity of chemical substances has been attempted as part of a safety test for chemical substances.

Estrogen binds to the estrogen receptor in an estrogen target cell so that the receptor is activated to bind to chromosomal estrogen response element sequences. A transcription coupling factor, which recognizes the complex of the estrogen and the estrogen receptor, binds to the estrogen response element sequences to promote the expression of the genes downstream of the sequences. For the method of determining estrogen-like activity of chemical substances, therefore, there has been a need to develop an assay system for evaluating the ability of the chemical substances to regulate the estrogen receptor activity, and there has been a demand for an estrogen receptor gene which is applicable in such an assay system.

DISCLOSURE OF INVENTION

Under the circumstances, the inventors have made active investigations and succeeded in isolating an estrogen receptor gene from a reptile, whiptail lizard to complete the present invention.

The present invention is therefore directed to each of the following items:

1. An estrogen receptor gene, characterized by comprising a nucleotide sequence coding for any one of the following amino acid sequences (hereinafter such a gene may be referred to as the inventive gene):

<Amino Acid Sequence>

(a) the amino acid sequence of SEQ ID NO:1, (b) an amino acid sequence of a protein having an estrogen receptor activity, said amino acid sequence has at least 85% sequence identity with the amino acid sequence of SEQ ID NO:1, (c) an amino acid sequence encoded by the nucleotide sequence of SEQ ID NO:2, and (d) an amino acid sequence of a protein having an estrogen receptor activity, said amino acid sequence is encoded by a nucleotide sequence having at least 85% sequence identity with a DNA having the nucleotide sequence of SEQ ID NO:2;

2. An estrogen receptor gene, characterized by comprising the nucleotide sequence of SEQ ID NO:2;

3. A vector, characterized by comprising the estrogen receptor gene according to the above 1 (hereinafter such a vector may be referred to as the inventive vector);

4. The vector according to the above 3, characterized by further comprising a promoter operably linked to the estrogen receptor gene;

5. A method for producing a vector, characterized by comprising the step of incorporating the estrogen receptor gene according to the above 1 into a vector replicable in a host cell;

6. A transformant, characterized by being formed by introducing the estrogen receptor gene according to the above 1 in a host cell (hereinafter such a transformant may be referred to as the inventive transformant);

7. The transformant according to the above 6, wherein the estrogen receptor gene is located in a chromosome of the host cell;

8. The transformant according to the above 6, wherein the host cell is an animal cell or an yeast cell;

9. A method for producing a transformant, characterized by comprising the step of introducing the estrogen receptor gene according to the above 1 into a host cell;

10. A method for producing an estrogen receptor, characterized by comprising the steps of culturing the transformant according to the above 6 and collecting a produced estrogen receptor from the culture;

11. A DNA, characterized by comprising a partial nucleotide sequence of the estrogen receptor gene according to the above 1;

12. The DNA according to the above 11, wherein the partial nucleotide sequence is a nucleotide sequence coding for an amino acid sequence of a ligand binding domain of the estrogen receptor;

13. An estrogen receptor, characterized by comprising any one of the following amino acid sequences (hereinafter such an estrogen receptor may be referred to as the inventive estrogen receptor):

<Amino Acid Sequence>

(a) the amino acid sequence of SEQ ID NO:1, (b) an amino acid sequence of a protein having an estrogen receptor activity, said amino acid sequence has at least 90% sequence identity with the amino acid sequence of SEQ ID NO:1, (c) an amino acid sequence encoded by the nucleotide sequence of SEQ ID NO:2, and (d) an amino acid sequence of a protein having an estrogen receptor activity, said amino acid sequence is encoded by a nucleotide sequence having at least 90% sequence identity with a DNA having the nucleotide sequence of SEQ ID NO:2;

14. An estrogen receptor, characterized by comprising the amino acid sequence of SEQ ID NO:1;

15. A method for evaluating the ability of a test substance to regulate an estrogen receptor activity, characterized by comprising the steps of:

(1) bringing the test substance into contact with a transformant formed by introducing, into a host cell, the estrogen receptor gene according to the above 1 and a reporter gene linked downstream of a transcriptional control DNA including an estrogen response element sequence;

(2) determining an expression amount of the reporter gene of the transformant or an index value having a correlation to the expression amount; and (3) evaluating the ability of the substance to regulate the estrogen receptor activity based on the determined expression amount or the index value having a correlation to the expression amount;

16. A method for searching for a substance having the ability to regulate an estrogen receptor activity, characterized by comprising the step of selecting a substance for the ability to regulate the estrogen receptor activity based on the ability of regulating the estrogen receptor activity evaluated by the method according to the above 15;

17. A protein complex, characterized by comprising: a protein which comprises one of the elements from group I below (either A or B) and one of the elements from group II below (either X or Y); and a protein which comprises the other of the elements from group I below (either B or A) and the other of the elements from group II below (either Y or X), wherein both proteins form the complex under the control of the ligand (hereinafter such a protein complex may be referred to as the inventive protein complex), group I consisting of the following elements:

(A) an estrogen receptor binding region of a transcription coupling factor capable of binding, under the control of the ligand, to a transcription coupling factor binding region of the estrogen receptor according to the above 13; and (B) a transcription coupling factor binding region of the estrogen receptor capable of binding, under the control of the ligand, to an estrogen receptor binding region of a transcription coupling factor;

group II consisting of the following elements:

(X) a DNA binding region of a transcriptional control factor operable in a host cell; and (Y) a transcription activating domain of a transcriptional control factor operable in a host cell;

18. The protein complex according to the above 17, wherein element (X) from group II is capable of binding to a DNA comprising any one of the following nucleotide sequences:

<Nucleotide Sequence>

(1) a Gal protein-binding DNA nucleotide sequence (5'-CGGACAACTGTTGACCCG-3' (SEQ ID NO:22)), (2) a Lex protein-binding DNA nucleotide sequence (5'-TACTGTATGTACATACAGTA-3' (SEQ ID NO:23)), (3) a Lac I receptor protein-binding DNA nucleotide sequence (5'-GAATTGTGAGCGCGCACAATTC-3' (SEQ ID NO:24)), (4) a tetracycline receptor protein-binding DNA nucleotide sequence (5'-TCGAGTTTACCACTCCCTATCAGTGATA-GAGAAAAGTGAAAG-3' (SEQ ID NO:25)), (5) a ZFHD-1 protein-binding DNA nucleotide sequence (5'-TAATGATGGGCG-3' (SEQ ID NO:26)), and (6) an estrogen response nucleotide sequence (5'-GGT-CANNNTGACC-3' (SEQ ID NO:27));

19. The protein complex according to the above 17, wherein element (Y) from group II is derived from any one of the following proteins:

<Protein>

(1) Gal protein,
(2) Lex protein,
(3) Lac I receptor protein,
(4) a tetracycline receptor protein,
(5) ZFHD-1 protein,
(6) B42 protein, and
(7) a transcription coupling factor capable of binding, under the control of the ligand, to a transcription coupling factor binding region of the estrogen receptor according to the above 13;

20. The protein complex according to the above 17, wherein element (B) from group I has a domain to which the ligand binds;

21. A transformant, characterized by being formed by introducing, into a host cell, (1) one of the elements from group i below (either a or b) and one of the elements from group ii below (either x or y); (2) the other of the elements from group i below (either b or a) and the other of the elements from group ii below (either y or x); and (3) element iii below (hereinafter such a transformant may be referred to as the inventive protein complex gene introduced transformant), group i consisting of the following elements:

(a) an DNA having a nucleotide sequence coding for an amino acid sequence of an estrogen receptor binding region of a transcription coupling factor capable of binding, under the control of a ligand, to a transcription coupling factor binding region of an estrogen receptor having an amino acid sequence encoded by the nucleotide sequence of the estrogen receptor gene according to the above 1; and (b) a DNA having a nucleotide sequence coding for an amino acid sequence of a transcription coupling factor binding region of an estrogen receptor capable of binding, under the control of a ligand, to an estrogen receptor binding region of a transcription coupling factor;

group ii consisting of the following elements:

(x) a DNA having a nucleotide sequence coding for an amino acid sequence of a DNA binding region of a transcriptional control factor operable in a host cell; and (y) a DNA having a nucleotide sequence coding for an amino acid sequence of a transcription activating domain of a transcriptional control factor operable in a host cell;

element iii comprising:

a DNA to which a DNA binding region having an amino acid sequence encoded by the nucleotide sequence of element (x) from group ii is capable of binding; and a DNA having a reporter gene linked downstream of a promoter which can be activated by a transcription activating domain having an amino acid sequence encoded by the nucleotide sequence of element (y) from group ii;

22. The transformant according to the above 21, wherein element (x) from group ii is a DNA having a nucleotide sequence coding for an amino acid sequence of a protein which is capable of binding to a DNA comprising any one of the following nucleotide sequences:

<Nucleotide Sequence>

(1) a Gal protein-binding DNA nucleotide sequence (5'-CGGACAACTGTTGACCCG-3' (SEQ ID NO:22)), (2) a Lex protein-binding DNA nucleotide sequence (5'-TACTGTATGTACATACAGTA-3' (SEQ ID NO:23), (3) a Lac I receptor protein-binding DNA nucleotide sequence (5'-GAATTGTGAGCGCGCACAATTC-3' (SEQ ID NO:24), (4) a tetracycline receptor protein-binding DNA nucleotide sequence (5'-TCGAGTTTACCACTCCCTATCAGTGATA-GAGAAAAGTGAAAG-3' (SEQ ID NO:25), (5) a ZFHD-1 protein binding DNA nucleotide sequence (5'-TAATGATGGGCG-3' (SEQ ID NO:26)), and (6) an estrogen response nucleotide sequence (5'-GGT-CANNNTGACC-3' (SEQ ID NO:27));

23. The transformant according to the above 21, wherein element (y) from group ii is derived from a DNA having a nucleotide sequence coding for the amino acid sequence of any one of the following proteins:

<Protein>

(1) Gal protein,
(2) Lex protein,
(3) Lac I receptor protein,
(4) a tetracycline receptor protein,
(5) ZFHD-1 protein, (6) B42 protein, and (7) a transcription coupling factor capable of binding, under the control of a ligand, to a transcription coupling factor binding region of an estrogen receptor having an amino acid sequence encoded by the nucleotide sequence of the estrogen receptor gene according to the above 1;

24. The transformant according to the above 21, wherein element (b) from group i comprises a DNA having a nucleotide sequence coding for an amino acid sequence of a domain to which the ligand is capable of binding;

25. A method for evaluating the ability of a test substance to regulate an estrogen receptor activity, characterized by comprising:

(1) a first step of bringing the test substance into contact with the transformant according to the above 21;

(2) a second step of determining, after the first step, an expression amount of the reporter gene of the transformant or an index value having a correlation to the expression amount; and (3) a third step of evaluating the ability of the substance to regulate the estrogen receptor activity based on the determined expression amount or the index value having a correlation to the expression amount determined in the second step;

26. A method for searching for a substance having the ability to regulate an estrogen receptor activity, characterized by comprising the step of selecting a substance for the ability to regulate the estrogen receptor activity based on the ability of regulating the estrogen receptor activity evaluated by the method according to the above 25;

27. An agent for regulating an estrogen receptor activity, characterized by comprising the substance selected by the searching method according to the above 26 or a pharmaceutically acceptable salt thereof as an active component;

28. Use of the estrogen receptor gene according to the above 1 for a two-hybrid assay;

29. Use of the DNA according to the above 11 for a two-hybrid assay; and

30. A receptor binding assay, characterized by comprising the steps of:

(1) bringing a test substance into contact with the estrogen receptor according to the above 14 which is bound to a labeled ligand; and (2) monitoring the amount of a free form of the labeled ligand generated by competition between the labeled ligand and the test substance or a bound form of the labeled ligand or an index value having a correlation to the amount to indirectly identify the binding state between the estrogen receptor and the test substance (hereinafter such an assay may be referred to as the inventive receptor binding assay).

BEST MODE FOR CARRYING OUT THE INVENTION

Figure 1:
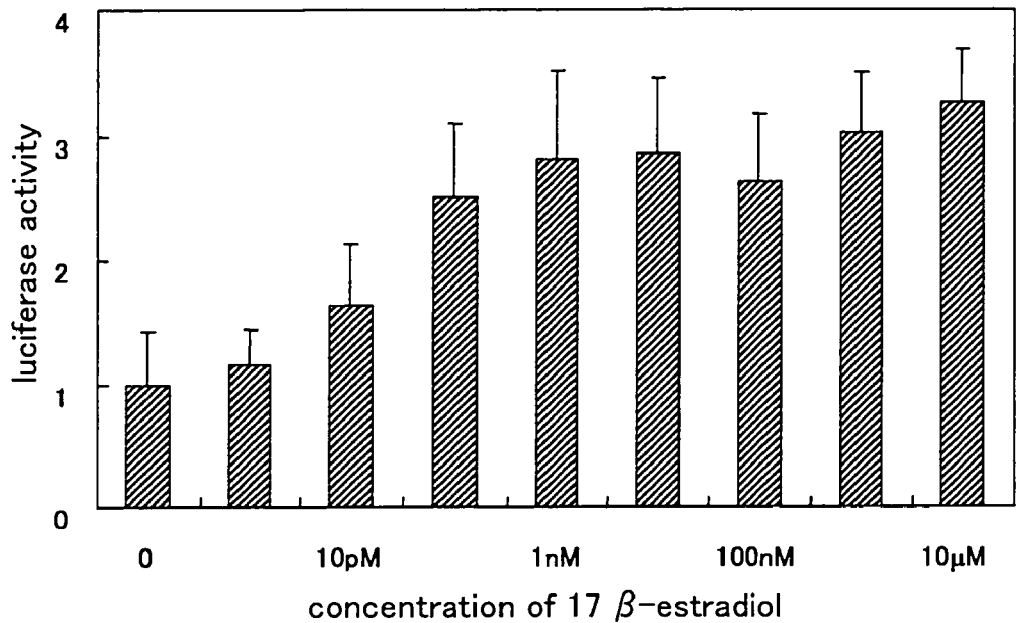
FIG. 1 is a diagram showing a result of determining the ability of E2 to regulate the estrogen receptor activity by the reporter assay using the inventive gene. The abscissa axis represents the concentration of E2 in each assay group. The left end column indicated by O corresponds to an assay group in which DMSO was added at a final concentration of 0.1% in place of the DMSO solution of E2 (E2-free group). The ordinate axis represents the luciferase activity value where the luciferase activity value of the E2-free group is normalized as 1.

The present invention is described in detail below.

The inventive gene comprises a nucleotide sequence or the like coding for any one of the following amino acid sequences: (a) the amino acid sequence of SEQ ID NO:1, (b) an amino acid sequence of a protein having an estrogen receptor activity, said amino acid sequence has at least 85% (preferably at least 90%) sequence identity with the amino acid sequence of SEQ ID NO:1, (c) an amino acid sequence encoded by the nucleotide sequence of SEQ ID NO:2, and (d) an amino acid sequence of a protein having an estrogen receptor activity, said amino acid sequence is encoded by a nucleotide sequence having at least 85% (preferably at least 90%) sequence identity with a DNA having the nucleotide sequence of SEQ ID NO:2.

Examples of the sequence (b) or (d) with "at least 85% sequence identity" include modifications or variations of the amino acid sequence of SEQ ID NO:1 which are caused by intracellular protein processing of the amino acid sequence, by natural variation depending on the species, individual difference, organ, tissue, and the like of the protein producing organism, or by artificial amino acid variation (such as amino acid variation in the amino acid sequence of a protein which is produced by the steps of causing variations in the DNA coding for the natural protein by site-directed mutagenesis or any other mutagenesis and allowing the expression of the DNA).

For example, the method for artificially causing the amino acid variation by deletion, addition, or substitution (hereinafter such variation may be generically called amino acid modification) include a process comprising the steps of carrying out conventional site-directed mutagenesis on the DNA including the nucleotide sequence coding for the amino acid sequence of SEQ ID NO:1 and then allowing the expression of the DNA by a conventional method. Examples of the site-directed mutagenesis process include a process using amber mutation (Gapped Duplex process)(Nucleic Acids Res., 12, 9441-9456, 1984) and a PCR technique using a mutagenesis primer.

At least one, specifically one to several (herein "several" means about 2 to about 10), or more amino acid residues may be modified in the above process. The amino acid residues may be modified in any numbers as far as the estrogen receptor activity can be developed.

Of the deletion, addition, and substitution, the substitution is particularly preferred in the amino acid modification. Amino acids that are similar to each other in hydrophobicity, charge, pK, stereo-structural feature, or the like are more preferably replaced with each other. For example, such substitutable amino acids are in each of the following groups: 1) glycine and alanine; 2) valine, isoleucine, and leucine; 3) aspartic acid, glutamic acid, asparagine, and glutamine; 4) serine and threonine; 5) lysine and arginine; and 6) phenylalanine and tyrosine.

As regards the present invention, "sequence identity" refers to identity and homology of sequences between two DNAs or two proteins. The sequence identity may be determined by comparing the two sequences, each aligned in an optimal state, over the whole region. The DNA or protein to be compared may include an added or deleted portion(s) (such as a gap portion) in the optimal alignment. For example, the sequence identity may be calculated using Vector NTI through the step of producing the alignment using ClustalW algorithm (Nucleic Acid Res., 22(22), 4673-4680, 1994). Specifically, the sequence identity may be determined using sequence analysis software such as Vector NTI, GENETYX-MAC, or any analysis tool available from any public database. For example, such a database is publicly available from the home page at http://www.ddbj.nig.ac.jp.

In the present invention, the sequence identity is preferably 90% or more with respect to the amino acid sequence and also preferably 90% or more with respect to the nucleotide sequence.

The DNA including the nucleotide sequence coding for the amino acid sequence (b) or (d) is hybridizable under a stringent condition with the DNA including the nucleotide sequence coding for the amino acid sequence (a). As regards the term "hybridizable under a stringent condition", for example, hybridization may be performed according to the conventional process such as the process disclosed in the text (Sambrook J., Frisch E. F., and Maniatis T., Molecular Cloning 2nd edition, Cold Spring Harbor Laboratory Press). For example, the "stringent condition" may be achieved through the steps of forming a hybrid in a solution containing 6×SSC (let the solution containing 1.5 M NaCl and 0.15 M trisodium citrate be 10×SSC) at 45° C. and then washing the hybrid with 2×SSC at 50° C. (Molecular Biology, John Wiley & Sons, N.Y. (1989), 6.3.1-6.3.6). The salt concentration for the washing step may be selected from the range of 2×SSC at 50° C. (a low stringency condition) to 0.2×SSC at 50° C. (a high stringency condition). The temperature of the washing step may be selected from the range of room temperature (a low stringency condition) to 65° C. (a high stringency condition). Both of the salt concentration and the temperature may be altered.

For example, the inventive gene may be obtained from the tissue of a reptile such as a squamatan including whiptail lizard (scientific name: *Cnemidophorus uniparens*) according to such a genetic engineering process as disclosed in the text (J. Sambrook, E. F. Frisch, and T. Maniatis, Molecular Cloning 2nd edition, Cold Spring Harbor Laboratory, 1989).

For example, first, total RNA is prepared from the tissue of a reptile such as a squamatan. Specifically, the tissue of a whiptail lizard such as a liver tissue is homogenized in a solution containing a protein denaturant such as guanidine hydrochloride and guanidine thiocyanate, and then phenol, chloroform or the like is added to the homogenate to denature the proteins. The denatured proteins are removed by centrifugation or the like as a precipitated fraction, and then the recovered supernatant fraction is extracted using a guanidine hydrochloride/phenol process, a SDS-phenol process, a guanidine thiocyanate/CsCl process, or the like to give total RNA. These processes may be performed using a commercially available kit, for example, including ISOGEN (Nippon Gene).

After the extraction, the total RNA is used as a template. An oligo-dT adapter primer, a random primer, a custom primer, or the like is allowed to anneal to the template, and then a single stranded cDNA is synthesized using a reverse transcriptase. These processes may be performed using a commercially available kit, for example, including TaKaRa RNA LA PCR™ Kit (AMV) Ver. 1.1 (Takara) and TaKaRa RNA PCR Kit (AMV) Ver. 2.1 (Takara). Examples of the custom primer include an oligonucleotide with a length of about 20 bp to about 40 bp, specifically an oligonucleotide including the nucleotide sequence from nucleotide 1722 to 1746 of the nucleotide sequence of SEQ ID NO:2, more specifically an oligonucleotide comprising the nucleotide sequence of SEQ ID NO:3 and an oligonucleotide comprising the nucleotide sequence of SEQ ID NO:4.

A template of the synthesized single stranded cDNA and a primer of an RNA, for example, obtained by inserting a nick and a gap into an RNA strand using *E. coli* RNaseH are. used to form a double stranded cDNA by means of *E. coli* DNA polymerase I. Both ends of the resulting double stranded cDNA are made blunt using T4 DNA polymerase. The double stranded cDNA with blunt ends is purified and recovered by a conventional process including phenol-chloroform extraction, ethanol precipitation and the like. In addition, the recovered double stranded cDNA may be ligated with a ligase into a vector such as plasmid pUC118 and phage λgt10 to form a cDNA library.

A template of the resulting double stranded cDNA or cDNA library and a primer of an oligonucleotide, for example, including a partial nucleotide sequence of the SEQ ID NO:2 sequence are used to form the inventive gene by performing polymerase chain reaction (hereinafter referred to as PCR). Examples of the primer for use in PCR include an oligonucleotide with a length of about 20 bp to about 40 bp such as an oligonucleotide including any nucleotide sequence selected from the 5'-terminal region of the SEQ ID NO:2 nucleotide sequence and an oligonucleotide including a nucleotide sequence complementary to any nucleotide sequence selected from the 3'-terminal region of the SEQ ID NO:2 nucleotide sequence. Specifically, examples of the forward primer include an oligonucleotide including the nucleotide sequence from nucleotide 1 to 25 of the SEQ ID NO:2 nucleotide sequence, more specifically an oligonucleotide comprising the nucleotide sequence of SEQ ID NO:5 and an oligonucleotide comprising the nucleotide sequence of SEQ ID NO:6. Examples of the reverse primer include an oligonucleotide including a nucleotide sequence complementary to the nucleotide sequence from nucleotide 1722 to 1746 of the SEQ ID NO:2 sequence, more specifically an oligonucleotide comprising the nucleotide sequence of SEQ ID NO:3 and an oligonucleotide comprising the nucleotide sequence of SEQ ID NO:4. For example, PCR may be performed under the following conditions: 50 μl of a reaction solution containing 5 μl of 10×LA PCR buffer II ($Mg^{2+}$-free) (Takara), 5 μl of 25 mM $MgCl_2$, 8 μl of 2.5 mM dNTP mixture (wherein the mixture contains dATP, dGTP, dCTP, and dTTP at each content of 2.5 mM, and each of them is at a final concentration of 0.4 mM), 1 μl of 10 μM each primer (at each final concentration of 0.2 μM), 0.1 to 0.5 μg of the single stranded cDNA template, and 2.5 units of TaKaRa LA Taq (Takara); and 30 cycles of 94° C. for 1 minute, 50° C. for 5 minutes, 94° C. for 1 minute, 50° C. for 30 seconds, and 72° C. for 2.5 minutes.

Alternatively, the resulting cDNA library may be used to produce the inventive gene by a hybridization process using a DNA including, for example, a partial nucleotide sequence of the SEQ ID NO:2 sequence as a probe. For example, the probe may be a DNA or the like including the nucleotide sequence between nucleotides 1 to 126, 470 to 570, 690 to 1040, or 1624 to 1710 of the SEQ ID NO:2 nucleotide sequence. The hybridization may be performed under the following conditions: under a stringent condition, for example, in the presence of 6×SSC (0.9 M NaCl and 0.09 M sodium citrate), 5× Denhardt's solution (0.1% (w/v) Ficoll 400, 0.1% (w/v) polyvinylpyrrolidone, and 0.1% (w/v) BSA), 0.5% (w/v) SDS, and 100 μg/ml of denatured salmon sperm DNA or in a DIG EASY Hyb solution (Boehringer Mannheim) containing 100 μg/ml of denatured salmon sperm DNA, holding at 65° C., then in the presence of 1×SSC (0.15 M NaCl and 0.015 M sodium citrate) and 0.5% (w/v) SDS, holding at room temperature for 15 minutes twice, and in the presence of 0.1×SSC (0.015 M NaCl and 0.0015 M sodium citrate) and 0.5% (w/v) SDS, holding at 68° C. for 30 minutes.

The resulting inventive gene may be cloned into a vector according to such a genetic engineering process as disclosed in the text (J. Sambrook, E. F. Frisch, and T. Maniatis, Molecular Cloning 2nd edition, Cold Spring Harbor Laboratory, 1989). Specifically, for example, the cloning may be performed using TA cloning kit (Invitrogen) or a commercially available plasmid vector such as pBluescriptII (Stratagene).

Alternatively, based on the nucleotide sequence of SEQ ID NO:2, the inventive gene may be chemically synthesized by a conventional method such as a phosphite triester method (Hunkapiller, M. et al., Nature, 310, 105, 1984).

The nucleotide sequence of the resulting inventive gene may be confirmed by the Maxam-Gilbert method (for example, as disclosed in Maxam, A. M. & W. Gilbert, Proc. Natl. Acad. Sci. USA, 74, 560, 1977) or the Sanger method (for example, as disclosed in Sanger, F. & A. R. Coulson, J. Mol. Biol., 94, 441, 1975 or Sanger, F, & Nicklen and A. R. Coulson., Proc. Natl. Acad. Sci. USA, 74, 5463, 1977).

The inventive gene may be incorporated into a vector operable in a host cell (hereinafter referred to as the basic vector) according to a conventional genetic engineering process to form the inventive vector. For example, the basic vector contains genetic information replicable in the host cell, is self-multipliable, can be isolated or purified from the host cell, and has a detectable marker.

Examples of the basic vector applicable in constructing the inventive vector include: plasmid pUC119 (Takara) and phagemid pBluescriptII (Stratagene) each for an E. coli host cell; plasmids pGBT9, pGAD424, and pACT2 (Clontech) each for a budding yeast host cell; a plasmid such as pRc/RSV and pRc/CMV (Invitrogen), a virus-derived autonomous replication origin-containing vector such as bovine papilloma virus plasmid pBPV (Amersham Pharmacia Biotech) and EB virus plasmid pCEP4 (Invitrogen), and a virus such as vaccinia virus each for a mammal host cell; and an insect virus such as baculovirus for an insect host cell. When the autonomous replication origin-containing vector such as the plasmid pACT2 for the yeast, the bovine papilloma virus plasmid pBPV, and the EB virus plasmid pCEP4 is used to form the inventive vector, the vector introduced in the host cell is held in the form of an episome in the cell.

In order to incorporate the inventive gene into baculovirus or vaccinia virus, a transfer vector may be used, which contains a nucleotide sequence homologous to the virus genome to be used. Examples of such a transfer vector include plasmids such as pVL1392 commercially available from Pharmingen, pVL1393 (Smith, G. E., Summers M. D. et al., Mol. Cell. Biol., 3, 2156-2165, 1983), and pSFB5 (Funahashi, S. et al., J. Virol., 65, 5584-5588, 1991). When the inventive gene is introduced into the transfer vector and the vector and the virus genome are simultaneously introduced into the host cell, homologous recombination occurs between the vector and the virus genome so as to form a virus having the inventive gene incorporated in the genome. The virus genome may be a baculovirus, adenovirus, or vacciniavirus genome.

More specifically, in the process of incorporating the inventive gene into baculovirus, first, the inventive gene is inserted into a multicloning site of the transfer vector such as pVL1393 and pVL1392, and then the transfer vector DNA and Baculovirus genome DNA (Baculogold (Pharmingen)) are introduced into an insect cell line Sf21 (available from ATCC) by calcium phosphate method. The resulting cells are cultured, and then the culture is subjected to centrifugation and other processes so that viral particles are recovered, whose genome contains the inventive gene. The recovered viral particles are deproteinized with phenol or the like to give the inventive gene-containing virus genome. The resulting virus genome may be introduced into a host cell having the ability to form viral particles, such as insect cell line Sf21, by calcium phosphate method or the like. The resulting cells may be cultured so that the inventive gene-containing viral particles can be multiplied.

Alternatively, the inventive gene may be directly incorporated into a relatively small genome such as a mouse leukemia virus genome without using the transfer vector. For example, the inventive gene is incorporated into a cloning site of virus vector-DC(X) (Eli Gilboa et al., BioTechniques, 4, 504-512, 1986). The resulting inventive gene-containing virus vector may be introduced into a packaging cell such as Ampli-GPE (J. Virol., 66, 3755, 1992) to form viral particles which bear the inventive gene-containing virus genome.

A promoter operable in the host cell may be operably linked upstream of the inventive gene and incorporated into the basic vector to form the inventive vector, which is capable of expressing the inventive gene in the host cell. The term "operably linked" means that the promoter is linked to the inventive gene in such a manner that the inventive gene can be expressed under the control of the promoter in the inventive gene-containing host cell. Examples of the promoter operable in the host cell include DNAs that exhibit a promoter activity in the host cell. Such examples include: a lactose operon promoter (lacP), a tryptophan operon promoter (trpP), an arginine operon promoter (argP), a galactose operon promoter (galP), tac promoter, T7 promoter, T3 promoter, and a λ-phage promoter (λ-pL and λ-pR) each for an E. coli host cell; a Rous sarcoma virus (RSV) promoter, a cytomegalovirus (CMV) promoter, a early or late simian virus (SV40) promoter, and a mouse papilloma virus (MMTV) promoter each for an animal or fission yeast host cell; and ADH1 promoter for a budding yeast host cell. The ADH1 promoter can be prepared from yeast expression vector pAAH5 bearing ADH1 promoter and its terminator (available from Washington Research Foundation)(Ammerer et al., Method in Enzymology, 101 part, p.192-201) by a conventional genetic engineering method. ADH1 promoter is included in the subject matter of the United State Patent Application No. 299,733 for Washington Research Foundation, and licensing is required for its industrial or commercial application in the United State.

The basic vector may preliminarily contain the promoter operable in the host cell. When such a basic vector is used, the inventive gene may be inserted downstream of the promoter so as to be operably linked to the promoter. For example, the above plasmids pRc/RSV, pRc/CMV and the like have a cloning site downstream from the promoter operable in an animal cell. The inventive gene may be inserted into the cloning site to form a vector, which may be introduced into the animal cell to express the inventive gene. These plasmids preliminarily contain an SV40 autonomous replication origin (ori). Therefore, any of these plasmids may be introduced into a cultured cell transformed with an ori-deleted SV40 genome, such as a COS cell, so that large numbers of the plasmid can be copied in the cell, and therefore, the inventive gene incorporated in the plasmid can be expressed in a large amount. The above plasmid pACT2 for the yeast has the ADH1 promoter. Therefore, the inventive gene may be inserted downstream of the ADH1 promoter in the plasmid or a derivative thereof to form the inventive vector capable of expressing a large amount of the inventive gene in the budding yeast such as CG1945 (Clontech).

The constructed inventive vector may be introduced into the host cell to form the inventive transformant. Any conventional introducing process may be used depending on the host cell. For the introduction into an $E.$ $coli$ host cell, any conventional method may be used, for example, including calcium chloride method and electroporation method as disclosed in the text (J. Sambrook, E. F. Frisch and T. Maniatis, Molecular Cloning 2nd edition, Cold Spring Harbor Laboratory Press, 1989). The introduction of the vector into a mammal host cell or an insect host cell may be performed according to any general gene transfection method such as calcium phosphate method, DEAE dextran method, electroporation method, and lipofection method. For the introduction into an yeast host cell, for example, Yeast transformation kit (Clontech) may be used based on lithium method.

The introduction of the viral genome into the host cell via the viral vector can be made not only by any of the above general gene transfection methods but also by infecting the host cell with viral particles which carry the inventive gene-containing viral genome.

In order to select the inventive transformant, for example, a marker gene may be introduced into the host cell together with the inventive vector, and then the host cell may be cultured by any method depending on the characteristic of the marker gene. For example, the marker gene may be a drug resistance gene against a selection drug that has killing activity on the host cell, and the inventive vector-containing host cell may be cultured in a medium that contains the selection drug. Examples of the combination of the drug resistance gene and the selection drug include the combinations of a neomycin resistance gene and neomycin, a hygromycin resistance gene and hygromycin, and a blasticidin S resistance gene and blasticidin S. Alternatively, the marker gene may complement auxotrophy of the host cell, and the inventive gene-containing cell may be cultured in a minimal medium free of the nutrient concerning the auxotrophy. When the inventive vector is introduced into a host cell capable of expressing the inventive gene, the estrogen binding activity may be detected.

For example, the inventive transformant in which the inventive gene is located in the chromosome of the host cell is obtained as follows. The inventive vector and the marker-containing vector are each digested with a restriction enzyme or the like into a linear chain and then introduced into the host cell by any method as described above. The cell is cultured generally for several weeks and then selected based on the expression amount of the introduced marker gene to give a desired transformant. For example, the inventive vector which contains the drug resistance gene as the marker gene is introduced into the host cell by any method as described above. The cell is subcultured in a selection drug-containing medium for at least several weeks, and then the drug-resistant clone surviving in the form of a colony is subjected to pure culture, resulting in the inventive transformant in which the inventive gene is incorporated in the chromosome of the host cell. In order to confirm the incorporation of the inventive gene in the host cell chromosome, the genome DNA may be prepared from the cell by a conventional genetic engineering method, and then the inventive gene may be detected in the prepared genome DNA by PCR, Southern hybridization, or the like using a DNA comprising a partial nucleotide sequence of the introduced inventive gene as a primer or a probe. The transformant can be stored in a frozen state and then allowed to awake as needed. Therefore, not every experiment needs the transformant preparation, and tests can be performed using the transformant with the characteristics and the handling conditions checked in advance.

The resulting inventive transformant may be cultured to produce the estrogen receptor, which may be recovered from the culture to give the inventive estrogen receptor.

For example, the inventive transformant is a microorganism, and in such a case, the transformant may be cultured using any medium that appropriately contains any carbon source, any nitrogen source, any organic or inorganic salt, and the like each for general microorganism culture. The cultivation may be carried out according to any conventional method for general microorganisms, such as solid culture method and liquid culture method (such as rotary shaking culture, reciprocal shaking culture, jar fermenter culture, and tank culture). The culture temperature and the pH of the medium can be each selected from a certain range in which the microorganism can grow. For example, the culture is generally performed at a temperature of about 15° C. to about 40° C. at a pH of about 6 to about 8. The culture time period depends on various culture conditions but is generally from about one day to about five days. When the expression vector contains an inducible promoter such as a temperature-inducible promoter and an IPTG-inducible promoter, the induction time is preferably within one day and generally several hours.

On the other hand, the transformant may be an animal cell such as a mammal cell and an insect cell, and the transformant may be cultured using any medium for general cell culture. If the transformant is prepared using the selection drug, the culture is preferably performed in the presence of the selection drug. For example, the mammal cell may be cultured using a DMEM medium (Nissui) containing FBS at a final content of 10% at 37° C. under 5% $CO_2$ while the medium may be replaced with fresh one every several days. After the cells are grown in a confluent state, for example, an about 0.25% (w/v) trypsin-containing PBS solution is added so that the cells are separated and dispersed. The cells are then diluted several times and inoculated into a new plate and further cultured. Similarly, the insect cell may be cultured using any insect cell culture medium such as a 10% (v/v) FBS and 2% (w/v) Yeastlate-containig Grace's medium at a culture temperature of 25° C. to 35° C. If the cell tends to peel off the plate as in the case of Sf21 cell, the cells may be dispersed by pipetting and subcultured without using the trypsin solution. When the transformant contains the virus vector such as baculovirus, the culture is preferably terminated before the cell is killed and the cytoplasmic effect is observed, for example, up to 72 hours after the viral infection.

The inventive estrogen receptor produced by the inventive transformant may be recovered from the culture by any appropriate combination of conventional isolation or purification processes. For example, after the culture is completed, the transformant cells are collected by centrifugation or the like, and the collected cells are suspended in a general buffer such as a buffer comprising 20 mM HEPES pH7, 1 mM EDTA, 1 mM DTT, and 0.5 mM PMSF and then homogenized in a Polytron, a ultrasonic apparatus, a Dounce homogenizer, or the like. The resulting homogenate may be ultracentrifuged at several tens thousand×g for several tens minutes to about one hour, and then the supernatant fraction may be taken to give an inventive estrogen receptor-containing fraction. In addition, the supernatant fraction may be subjected to any type of chromatography such as ion exchange, hydrophobic, gel filtration, or affinity chromatography to give the inventive estrogen receptor in a further purified state. In this process, the inventive estrogen receptor-containing fraction may be identified by a DNA binding assay or the like using a probe of an oligonucleotide with a length of about 15 bp to about 200 bp including an estrogen response element sequence, a nucleotide sequence to which the estrogen receptor is capable of binding.

The resulting inventive estrogen receptor may be used in a receptor binding assay or the like for evaluating the ability or the amount of any test substance to bind to or bound to the estrogen receptor.

The inventive gene may be used in a reporter assay for evaluating the ability of any test substance to regulate the estrogen receptor activity.

The present invention is also directed to a method for evaluating the ability of a test substance to regulate an estrogen receptor activity, comprising the steps of:

(1) bringing the test substance into contact with a transformant formed by introducing, into a host cell, the inventive estrogen receptor gene and a reporter gene linked downstream of a transcriptional control DNA including an estrogen response element sequence;

(2) determining an expression amount of the reporter gene of the transformant or an index value having a correlation to the expression amount; and (3) evaluating the ability of the substance to regulate the estrogen receptor activity based on the determined expression amount or the determined index value.

The ability to regulate the estrogen receptor activity may include an agonistic activity and an antagonistic activity on the estrogen receptor.

In the evaluating method, the "reporter gene linked downstream of a transcriptional control region including an estrogen response element sequence" may be a reporter gene linked downstream of a transcriptional control region or the like of the Xenopus Vitellogenin gene including the estrogen response element sequence or a reporter gene linked downstream of a transcriptional control region which includes a consensus sequence (5'-AGGTCAnnnTGACCTT-3' wherein n represents A, G, C, or T) of the estrogen response element sequence and a nucleotide sequence necessary for transcription initiation. Such a reporter gene may be used for monitoring the ability of the estrogen receptor to control transcription in the host cell. The reporter gene may be a luciferase gene, a secretory alkaline phosphatase gene, a β-galactosidase gene, a chloramphenicol acetyltransferase gene, a growth hormone gene, or the like. A preferred reporter protein encoded by the reporter gene is relatively stable in the host cell.

The inventive gene and the reporter gene linked downstream of the transcriptional control region including the estrogen response element sequence are introduced into the host cell (an estrogen receptor-absent host cell or the like such as HeLa, CV-1, Hepal, NIH3T3, HepG2, COS1, BF-2, and CHH-1 cells) to form a transformant. As described above, the inventive gene may be operably linked to the promoter operable in the host cell and incorporated in the basic vector before introduced into the host cell. The reporter gene linked downstream of the transcriptional control region including the estrogen response element sequence may also incorporated in the basic vector before use. For example, both of the reporter gene-containing vector in which the reporter gene is linked downstream of the transcriptional control region including the estrogen response element sequence and the inventive gene-containing vector in which the inventive gene is operably linked to the promoter operable in the host cell are introduced into the host cell together with the marker gene-containing vector. After the cell is cultured generally for several weeks, the desired transformant is selected based on the expression amount of the introduced marker gene. In the resulting transformant, the reporter gene linked downstream of the transcriptional control region including the estrogen response element sequence and the inventive gene operably linked to the operable promoter are incorporated in the host cell chromosome. In order to check whether the inventive gene is incorporated in the host cell chromosome, the genome DNA may be prepared from the cell by any conventional genetic engineering method, and then the inventive gene may be detected in the prepared genome DNA by PCR, Southern hybridization, or the like using a DNA including a partial nucleotide sequence of the introduced inventive gene as a primer or a probe. The transformant can be stored in a frozen state and then allowed to awake as needed. Therefore, the transformant preparation does not have to be made at every experiment, and tests can be performed using the transformant with the characteristics and the handling conditions checked in advance. The transformant will therefore be useful in a large scale screening with an automatic robot.

The resulting transformant is brought into contact with a test substance, for example, for several hours to several days or specifically, cultured in a test substance-containing medium for several hours to several days. A measurement is then made on the expression amount of the reporter gene of the transformant or an index value having a correlation to the amount. If the test substance (with an estrogen-like activity) binds to the estrogen receptor produced by the transformant and activates it, the transcription of the reporter gene will be promoted so that the reporter protein encoded by the reporter gene can be stored in the transformant cell or secreted into the medium. The amount of the reporter protein or the index value having a correlation to the amount is determined so that the expression amount of the reporter gene or the index value having a correlation to the amount can be determined per transformant cell. For example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase in the crude cell extract. Therefore, the intensity of the luminescence may be measured using a measuring apparatus such as a luminometer so that the amount of the luciferase and therefore the expression amount of the luciferase gene can be determined. In a similar manner, under the condition that the transformant is not in contact with the test material, a measurement is made on the expression amount of the reporter gene or the index value having a correlation to the amount. The measured expression amount or the index value is compared with the amount or the value measured under the test substance contact condition, so that the ability of the test substance to regulate the estrogen receptor activity (the agonistic activity on the estrogen receptor in this case) can be evaluated. On the other hand, for example, under each of the condition that the transformant is in contact with the estrogen such as 17β-estradiol (hereinafter referred to as E2) and the condition that the transformant is in contact with the estrogen and the test substance at the same time, a measurement is made on the expression amount of the reporter gene or the index value having a correlation to the amount in a similar manner to the above. The measurements under both conditions are compared with each other. If the expression amount or the index value under the latter condition is lower than that under the former condition, the test material can be evaluated as having the ability to regulate the estrogen receptor activity (the antagonistic activity on the estrogen receptor in this case).

By the above method, the substance having the ability to regulate the estrogen receptor activity can easily be selected based on the evaluation.

Based on the expression amount of the intracellular reporter gene or the index value having a correlation to the amount, the inventive gene or a DNA including a partial nucleotide sequence of the inventive gene may be applied to an assay system for detecting the ability to form a complex of two types of fusion proteins (two-hybrid) and the ability of the complex to regulate the transcription (two hybrid system, Nishikawa et al., Toxicol. Appl. Pharmacol., 154, 76-83, 1999). In this regard, the present invention is also directed to: a protein complex (the inventive protein complex); a transformant (the inventive protein complex gene introduced transformant);

a method for evaluating the ability of a test substance to regulate an estrogen receptor activity, comprising:

(1) a first step of bringing the test substance into contact with the inventive protein complex gene introduced transformant;

(2) a second step of determining, after the first step, an expression amount of the reporter gene of the transformant or an index value having a correlation to the expression amount; and (3) a third step of evaluating the ability of the substance to regulate the estrogen receptor activity based on the expression amount or the index value determined in the second step;

a method for searching for a substance having the ability to regulate an estrogen receptor activity, comprising the step of selecting a substance for the ability to regulate the estrogen receptor activity based on the ability evaluated by the above evaluating method; and an agent for regulating an estrogen receptor activity, comprising the substance selected by the above searching method or a pharmaceutically acceptable salt thereof as an active component.

As regards the inventive protein complex, examples of the transcription coupling factor including element (A) from group I include transcription coupling factors that are capable of recognizing the complex of the inventive estrogen receptor and the ligand and capable of binding to the complex, such as SRC1/NCoA1 (Onate, S. A. et al., Science, 1995, 270, 1354) and TIF2/GRIP1 (Voegel J. J. et al., EMBO J., 1996, 15, 3667). Examples of the estrogen receptor including element (B) from group I include estrogen receptors that are capable of binding to the above transcription coupling factor. In this case, such estrogen receptors have a ligand binding domain for forming the complex with the ligand. The DNA including a nucleotide sequence coding for the amino acid sequence of such a region may be a partial nucleotide sequence of the inventive gene, for example, including a DNA that includes a nucleotide sequence coding for the ligand binding domain of the estrogen receptor out of the inventive gene nucleotide sequence and excludes the nucleotide sequence coding for the amino acid sequence of element (X) from group II. Specifically, such a DNA may be a nucleotide sequence that includes at least the nucleotide sequence from nucleotide 877 to 1623 out of the SEQ ID NO:2 nucleotide sequence and excludes the nucleotide sequence from nucleotide 1 to 762 of the SEQ ID NO:2 nucleotide sequence. More specifically, such a DNA may include the nucleotide sequence from nucleotide 763 to 1746 of the SEQ ID NO:2 nucleotide sequence.

Examples of the transcriptional control factor including element (X) from group II include transcriptional control factors that are operable in the host cell and capable of binding to a DNA comprising any one of: a Gal protein-binding DNA nucleotide sequence (5'-CGGACAACTGTTGAC-CCG-3' (SEQ ID NO:22)), a Lex protein-binding DNA nucleotide sequence (5'-TACTGTATGTACATACAGTA-3' (SEQ ID NO:23), a Lac I receptor protein-binding DNA nucleotide sequence (5'-GAATTGTGAGCGCGCA-CAATTC-3' (SEQ ID NO:24), a tetracycline receptor protein-binding DNA nucleotide sequence (5'-TCGAGTTTAC-CACTCCCTATCAGTGATAGAGAAAAGTGAAAG-3' (SEQ ID NO:25), a ZFHD-1 protein binding DNA nucleotide sequence (5'-TAATGATGGGCG-3' (SEQ ID NO:26)), and an estrogen response element nucleotide sequence (5'-GGT-CANNNTGACC-3' (SEQ ID NO:27)). Examples of the transcriptional control factor including element (Y) from group II include transcriptional control factors that are operable in the host cell and are derived from any one of: Gal protein, Lex protein, Lac I receptor protein, a tetracycline receptor protein, ZFHD-1 protein, B42 protein, and a transcription coupling factor capable of binding, under the control of the ligand, to a transcription coupling factor binding region of the inventive estrogen receptor.

The protein complex comprising such elements may be produced by the inventive protein complex gene introduced transformant or the like.

As regards the inventive protein complex gene introduced transformant, element (a) from group i corresponds to a DNA that includes the nucleotide sequence coding for the amino acid sequence of element (A) from group I, and such a DNA may be prepared from the transcription coupling factor gene including element (A) from group I by any conventional genetic engineering technique. Element (b) from group i corresponds to a DNA that includes the nucleotide sequence coding for the amino acid sequence of element (B) from group I, and such a DNA may be prepared from the estrogen receptor gene including element (B) from group I by any conventional genetic engineering technique.

Element (x) from group ii corresponds to a DNA that includes the nucleotide sequence coding for the amino acid sequence of element (X) from group II, and such a DNA may be prepared from the transcription coupling factor gene including element (A) from group I by any conventional genetic engineering technique. Element (y) from group ii corresponds to a DNA that includes the nucleotide sequence coding for the amino acid sequence of element (Y) from group I, and such a DNA may be prepared from the estrogen receptor gene including element (Y) from group II by any conventional genetic engineering technique.

Element iii corresponds to a DNA including both of a DNA to which element (X) from group II is capable of binding and a DNA which includes a reporter gene linked downstream of a promoter capable of being activated by element (Y) from group II. The reporter gene may be any conventional reporter assay gene such as a luciferase gene, a secretory alkaline phosphatase gene, a β-galactosidase gene, a chloramphenicol acetyltransferase gene, and a growth hormone gene. A preferred reporter protein encoded by the reporter gene is relatively stable in the host cell. Examples of the DNA to which element (X) from group II is capable of binding include DNAs comprising any one of: a Gal protein-binding DNA nucleotide sequence (5'-CGGACAACTGTTGACCCG-3' (SEQ ID NO:22)), a Lex protein binding DNA nucleotide sequence (5'-TACTGTATGTACATACAGTA-3' (SEQ ID NO:23), a Lac I receptor protein binding DNA nucleotide sequence (5'-GAATTGTGAGCGCGCACAATTC-3' (SEQ ID NO:24), a tetracycline receptor protein binding DNA nucleotide sequence (5'-TCGAGTTTACCACTCCCTAT-CAGTGATAGAGAAAAGTGAAAG-3' (SEQ ID NO:25), a ZFHD-1 protein binding DNA nucleotide sequence (5'-TAATGATGGGCG-3' (SEQ ID NO:26)), and an estrogen response element nucleotide sequence (5'-GGTCANNNT-GACC-3' (SEQ ID NO:27)). For example, the promoter capable of being activated by element (Y) from group II may be an yeast-derived minimal TATA box sequence in the case that element (Y) from group II is derived from Gal protein.

The transformant may be produced by the steps of inserting, into a vector, an appropriate combination of the respective elements for expressing the inventive protein complex and introducing the resulting vector into a host cell by a conventional genetic engineering technique. In this process, element iii may stand independent, and two chimera genes 1 and 2 may be produced as follows: Chimera gene 1 is produced by the steps of adjusting the reading frames of the two nucleotide sequences: one of the elements from group i (a or b) and one of the elements from group ii (x or y) and linking the two nucleotide sequences to each other; Chimera gene 2 is produced by the steps of adjusting the reading frames of the two nucleotide sequences: the other of the elements from group i (b or a) and the other of the elements from group ii (y or x) and linking the two nucleotide sequences to each other. Chimera genes 1 and 2 may be each linked downstream of the promoter operable in a host cell, and in such a state, the respective elements may be introduced into a host cell. For the budding yeast host cell, the promoter may be an inducible promoter such as GAL1 promoter or a constant expression promoter such as ADH promoter. If the host cell contains an available intrinsic reporter gene, such a reporter gene may be used, and the introduction of a new reporter gene may be omitted.

For example, the host cell for forming the inventive protein complex gene introduced transformant may be a budding yeast cell, a mammal cell such as a HeLa cell, or the like. The host cell is preferably an estrogen receptor-absent cell in terms of good precision in determining the ability of the test substance to regulate the estrogen activity on the inventive estrogen receptor.

As regards the above evaluating method, the ability to regulate the estrogen receptor activity may include an agonistic activity and an antagonistic activity on the estrogen receptor.

In the evaluating method, the transformant is brought into contact with a test substance, for example, for several hours to several days, or specifically, cultured in a test substance-containing medium for several hours to several days. A measurement is then made on the expression amount of the reporter gene of the transformant or an index value having a correlation to the amount. If the test substance (with an estrogen-like activity) binds to the estrogen receptor produced by the transformant and activates it, the transcription of the reporter gene will be promoted so that the reporter protein encoded by the reporter gene can be stored in the transformant cell or secreted into the medium. The amount of the reporter protein or the index value having a correlation to the amount is determined so that the expression amount of the reporter gene or the index value having a correlation to the amount can be determined per transformant cell.

Specifically, for example, a luciferase reporter gene is used, and luciferin, the substrate of the luciferase, is added to a crude cell extract prepared from the transformant that has been in contact with the test substance, so that luminescence can be observed in an intensity proportional to the amount of the luciferase in the crude cell extract. Therefore, the intensity of the luminescence may be measured using a measuring apparatus such as a luminometer so that the amount of the luciferase and therefore the expression amount of the luciferase gene can be determined. In a similar manner, under the condition that the transformant is not in contact with the test material, a measurement is made on the expression amount of the reporter gene or the index value having a correlation to the amount. The measured expression amount or the index value is compared with the amount or the value measured under the test substance contact condition, so that the ability of the test substance to regulate the estrogen receptor activity (the agonistic activity on the estrogen receptor in this case) can be evaluated. On the other hand, for example, under each of the condition that the transformant is in contact with the estrogen such as 17β-estradiol (hereinafter referred to as E2) and the condition that the transformant is in contact with the estrogen and the test substance at the same time, a measurement is made on the expression amount of the reporter gene or the index value having a correlation to the amount in a similar manner to the above. The measurements under both conditions are compared with each other. If the expression amount or the index value under the latter condition is lower than that under the former condition, the test material can be evaluated as having the ability to regulate the estrogen receptor activity (the antagonistic activity on the estrogen receptor in this case).

By the above method, the substance having the ability to regulate the estrogen receptor activity can easily be selected based on the evaluation. Therefore, the present invention is also directed to an agent for regulating an estrogen receptor activity, containing such a substance or a pharmaceutically acceptable salt thereof as an active component.

The present invention is also directed to the use of the inventive estrogen receptor gene;

the use of the inventive estrogen receptor gene for a two-hybrid assay; and the use of a DNA including a partial nucleotide sequence of the inventive estrogen receptor gene for a two-hybrid assay. The system for the two-hybrid assay may be formed using a commercially available kit such as Matchmaker Two-hybrid System (Clontech) and CheckMate Mammalian Two-Hybrid System (Promega). For example, the system for the two-hybrid assay may comprises a transformant formed by the step of introducing genes (1) and (2) below into budding yeast Y190 strain (Clontech) which has intrinsic GALL UAS (upstream activating sequence) and LacZ gene (reporter gene) linked downstream of an yeast-derived minimal TATA box sequence.

(1) A chimera gene including a nucleotide sequence which is linked downstream of the ADH1 promoter and codes for the amino acid sequence of a fusion protein comprising a DNA binding region of GAL4 protein and the transcription coupling factor binding region of the inventive estrogen receptor having the ligand binding domain.

(2) A chimera gene including a nucleotide sequence which is linked downstream of the ADH1 promoter and codes for the amino acid sequence of a fusion protein comprising a transcription activating domain of GAL4 protein and an estrogen receptor binding region of the transcription coupling factor TIF2 capable of recognizing the complex of the inventive estrogen receptor and the ligand and binding to the complex.

While the transformant is cultured, for example, for several hours to several days, the test substance is added to the medium to be brought into contact with the transformant. The reporter gene or an index value having a correlation thereto is measured to examine the transcriptional control ability of the protein complex formed through the binding of the estrogen receptor binding region and the transcription coupling factor, which recognizes the complex of the inventive estrogen receptor and the ligand and binds to the complex.

The present invention is also directed to a receptor binding assay (the inventive receptor binding assay).

The inventive receptor binding assay enables the measurement of the ability of any chemical substance to bind to the inventive estrogen receptor, the quantification of the binding amount, and the analysis of the binding specificity or the binding strength. For example, a labeled ligand is preliminarily allowed to bind to the inventive estrogen receptor, which is recovered from the inventive transformant as described above. The test material is then allowed to coexist with the labeled ligand so that the test substance competes with the labeled ligand. Depending on the affinity of each for the inventive estrogen receptor, the labeled ligand is released from the receptor. The amount of the labeled ligand bound to the receptor decreases, and therefore, the amount of the label bound to the receptor decreases. Thus, the label amount of the free form or the bound form of the labeled ligand may be monitored to indirectly determine the binding state between the inventive estrogen receptor and the test substance. For example, such a process enables the measurement of the ability of the test substance to bind to the inventive estrogen receptor.

For example, the labeled ligand may be tritium-labeled E2 or the like. The bound and free forms of the labeled ligand may be separated by hydroxyapatite method, glycerol density gradient ultracentrifugation or the like. The reaction system may broadly be classified into three groups. The first group includes a system in which only a solvent is added to the labeled ligand-bound inventive estrogen receptor and corresponds to the system in which the addition amount of the test substance is zero. In this system, the label amount of the bound form of the labeled ligand represents the total amount of the labeled ligand bound to the inventive estrogen receptor (the total binding amount). The second group includes a system in which for example, an unlabeled ligand is added to the labeled ligand-bound inventive estrogen receptor in such a concentration that the inventive estrogen receptor is saturated with the unlabeled ligand so as to have no capacity for binding to the labeled ligand (for example, 10 μM). In this system, the label amount of the bound form of the labeled ligand is determined as the amount of the labeled ligand nonspecifically bound to the inventive estrogen receptor (the nonspecific binding amount). Therefore, the amount of the labeled ligand specifically bound to the inventive estrogen receptor (the specific binding amount) is calculated by subtracting the nonspecific binding amount from the total binding amount. The third group includes a system in which the test substance is added to the labeled ligand-bound inventive estrogen receptor at a final concentration of 10 μM, for example (such a concentration may arbitrarily be altered depending on the purpose). If the test substance has the ability to bind to the estrogen receptor, the label amount of the bound form of the labeled ligand obtained in this system will be smaller than the specific binding amount obtained as described above under the condition that the addition amount of the test material is zero. Thus, the binding state between the inventive estrogen receptor and the test substance is indirectly determined. The inventive receptor binding assay may be performed to determine the ability of the test substance to bind to the inventive estrogen receptor. If the test substance include different substances, the assay can also determine whether the test substance includes any substance that has an affinity for the inventive estrogen receptor. If the ability of the test substance to bind to the inventive estrogen receptor should be evaluated in a more detailed manner, for example, the test substance may be added at different concentrations in the third group in the process of the inventive receptor binding assay. For example, the label amount of the bound form of the labeled ligand may be determined to produce the amounts of the bound and free forms of the ligand, respectively, and then the results may be subjected to the Scatchard analysis so that the binding affinity, the binding specificity, the binding capacity, or the like can be evaluated between the test substance and the inventive estrogen receptor.

The inventive reporter assay, the two-hybrid system-related invention, and the inventive receptor binding assay can be applied to safety evaluation of chemical substances, detection of environmental estrogen-like substances, and the like.

EXAMPLES

The present invention is more specifically described with reference to the examples below, but such examples are not intended to limit the scope of the present invention.

Example 1

Preparation of the Inventive Gene

From liver tissue of whiptail lizard (scientific name: Cnemidophorus uniparens), total RNA was prepared using Trizol reagent (GIBCO-BRL) according to the product manual for the reagent. The resulting total RNA was used as a template, and an oligonucleotide comprising the nucleotide sequence of SEQ ID NO:7 was used as a primer. From these materials, a single stranded cDNA was synthesized using TaKaRa RNA LA PCR™ Kit (AMV) Ver. 1.1 (Takara) according to the protocol provided in the description (hereinafter the synthesized single stranded cDNA is referred to as single stranded cDNA7). Additionally, another oligonucleotide comprising the nucleotide sequence of the SEQ ID NO:14 was used as a primer in place of the oligonucleotide comprising the SEQ ID NO:7, and another single stranded cDNA was similarly synthesized (hereinafter the other synthesized single stranded cDNA is referred to as single stranded cDNA14).

PCR was then performed using an oligonucleotide comprising the nucleotide sequence of SEQ ID NO:9 and an oligonucleotide comprising the nucleotide sequence of SEQ ID NO:7 as primers and using single stranded cDNA7 as a template. The PCR reaction solution was prepared to contain per 50 µl: 5 µl of 10×LA PCR buffer II ($Mg^{2+}$-free, Takara), 5 µl of 25 mM $MgCl_2$, 8 µl of 2.5 mM dNTP mixture (wherein the mixture contained dATP, dGTP, dCTP, and dTTP at each content of 2.5 mM, and each of them was at a final concentration of 0.4 mM), 1 µl of 10 µM each primer (at each final concentration of 0.2 µM), 0.1 µg of single stranded cDNA7, and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes. After the thermal cycles, the reaction solution was subjected to electrophoresis using 1% low melting point agarose (AgaroseL, Nippon Gene), and a DNA of about 920 bp was recovered (hereinafter the resulting DNA is referred to as DNA97).

PCR was also performed using an oligonucleotide comprising the nucleotide sequence of SEQ ID NO:10 and an oligonucleotide comprising the nucleotide sequence of SEQ ID NO:11 as primers and using single stranded cDNA14 as a template under the above conditions. PCR was then further performed using the oligonucleotide comprising the nucleotide sequence of SEQ ID NO:10 and an oligonucleotide comprising the nucleotide sequence of SEQ ID NO:12 as primers. The PCR reaction solution was prepared to contain per 50 µl: 5 µl of the reaction solution obtained after the former PCR, 5 µl of 10×LA PCR buffer II ($Mg^{2+}$-free, Takara), 5 µl of 25 mM $MgCl_2$, 8 µl of 2.5 mM dNTP mixture (wherein the mixture contained dATP, dGTP, dCTP, and dTTP at each content of 2.5 mM, and each of them was at a final concentration of 0.4 mM), 1 µl of 10 µM each primer (at each final concentration of 0.2 µM), and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes. After the thermal cycles, the reaction solution was subjected to electrophoresis using 1% low melting point agarose (AgaroseL, Nippon Gene), and a DNA of about 790 bp was recovered (hereinafter the resulting DNA is referred to as DNA1012).

PCR was also performed using an oligonucleotide comprising the nucleotide sequence of SEQ ID NO:9 and an oligonucleotide comprising the nucleotide sequence of SEQ ID NO:8 as primers and using single stranded cDNA8 as a template under the above conditions. PCR was then further performed using an oligonucleotide comprising the nucleotide sequence of SEQ ID NO:13 and the oligonucleotide comprising the nucleotide sequence of SEQ ID NO:8 as primers. The PCR reaction solution was prepared to contain per 50 µl: 5 µl of the reaction solution obtained after the former PCR, 5 µl of 10×LA PCR buffer II ($Mg^{2+}$-free, Takara), 5 µl of 25 mM $MgCl_2$, 8 µl of 2.5 mM dNTP mixture (wherein the mixture contained dATP, dGTP, dCTP, and dTTP at each content of 2.5 mM, and each of them was at a final concentration of 0.4 mM), 1 µl of 10 µM each primer (at each final concentration of 0.2 µM), and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes. After the thermal cycles, the reaction solution was subjected to electrophoresis using 1% low melting point agarose (AgaroseL, Nippon Gene), and a DNA of about 650 bp was recovered (hereinafter the resulting DNA is referred to as DNA138).

The recovered three DNAs (DNA97, DNA1012, and DNA 138) were each cloned into a TA cloning vector (PGEM-T Easy Vector Systems, Promega), and then each plasmid contained in each resulting clone was subjected to sequence analysis. As a result, it was found that: DNA97 had the nucleotide sequence from nucleotide 616 to 1537 of the SEQ ID NO:2 sequence; DNA1012 had the nucleotide sequence from nucleotide 1 to 758 of the SEQ ID NO:2 sequence; and DNA138 had the nucleotide sequence from nucleotide 1056 to 1746 of the SEQ ID NO:2 sequence. These nucleotide sequences were linked to each other with the same parts overlapped, so that the nucleotide sequence of SEQ ID NO:2 was obtained, and such a nucleotide sequence was found to encode the amino acid sequence of SEQ ID NO:1.

Example 2

Construction of the Inventive Vector

At 37° C., 2 µg of DNA plasmid pRc/RSV (Invitrogen) with an RSV promoter was digested with restriction enzyme Spe I (10U) for 3 hours. To the resulting digest was added 5U of an alkaline phosphatase (BAP) and allowed to react at 60° C. for one hour. The resulting reaction product was then subjected to electrophoresis using 1% low melting point agarose (AgaroseL, Nippon Gene), and a DNA with a length of 5 to 6 kbp was recovered and used as a vector DNA.

On the other hand, PCR was performed using an oligonucleotide comprising the nucleotide sequence of SEQ ID NO:6 and an oligonucleotide comprising the nucleotide sequence of SEQ ID NO:7 as primers and using single stranded cDNA14 produced in Example 1 as a template. The PCR reaction solution was prepared to contain per 50 µl: 5 µl of 10×LA PCR buffer II ($Mg^{2+}$-free, Takara), 5 µl of 25 mM $MgCl_2$, 8 µl of 2.5 mM dNTP mixture (wherein the mixture contained DATP, dGTP, dCTP, and dTTP at each content of 2.5 mM, and each of them was at a final concentration of 0.4 mM), 1 µl of 10 µM each primer (at each final concentration of 0.2 µM), 0.1 µg of single stranded cDNA14, and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes.

PCR was also performed using an oligonucleotide comprising the nucleotide sequence of SEQ ID NO:6 and an oligonucleotide comprising the nucleotide sequence of SEQ ID NO:11 as primers. The PCR reaction solution was prepared to contain per 50 µl: 5 µl of the reaction solution obtained after the former PCR, 5 µl of 11×LA PCR buffer II ($Mg^{2+}$-free, Takara), 5 µl of 25 mM $MgCl_2$, 8 µl of 2.5 mM dNTP mixture (wherein the mixture contained dATP, dGTP, dCTP, and dTTP at each content of 2.5 mM, and each of them was at a final concentration of 0.4 mM), 1 µl of 10 µM each primer (at each final concentration of 0.2 µM), and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes. After the thermal cycles, the reaction solution was subjected to electrophoresis using 1% low melting point agarose (AgaroseL, Nippon Gene), and a DNA of about 1050 bp was recovered (hereinafter the resulting DNA is referred to as DNA611).

PCR was also performed using an oligonucleotide comprising the nucleotide sequence of SEQ ID NO:9 and an oligonucleotide comprising the nucleotide sequence of SEQ ID NO:4 as primers and using single stranded cDNA14 as a template under the above conditions. PCR was then further performed using the oligonucleotide comprising the nucleotide sequence of SEQ ID NO:21 and an oligonucleotide comprising the nucleotide sequence of SEQ ID NO:4 as primers. The PCR reaction solution was prepared to contain per 50 µl: 5 µl of the reaction solution obtained after the former PCR, 5 µl of 10×LA PCR buffer II ($Mg^{2+}$-free, Takara), 5 µl of 25 MM $MgCl_2$, 8 µl of 2.5 mM dNTP mixture (wherein the mixture contained dATP, dGTP, dCTP, and dTTP at each content of 2.5 mM, and each of them was at a final concentration of 0.4 mM), 1 µl of 10 µM each primer (at each final concentration of 0.2 µM), and 2.5 units of TaKaRa LA Taq (Takara). The reaction solution was kept at 94° C. for 2 minutes, and then at 50° C. for 5 minutes, and further subjected to 30 cycles each of which comprised keeping at 94° C. for 1 minute, 50° C. for 30 seconds, and then 72° C. for 2.5 minutes. After the thermal cycles, the reaction solution was subjected to electrophoresis using 1% low melting point agarose (AgaroseL, Nippon Gene), and a DNA of about 1120 bp was recovered (hereinafter the resulting DNA is referred to as DNA214).

Recovered DNA611 and DNA214 were each digested with restriction enzymes Spe I and Hinc II at 37° C. overnight. The resulting digests were each subjected to electrophoresis using 1% low melting point agarose (AgaroseL, Nippon Gene), and a DNA of about 1040 bp (the digest of DNA611) and a DNA of about 740 bp (the digest of DNA214) were recovered. The recovered two DNAs were mixed with the vector DNA, which was prepared as described above, and the mixture was subjected to a ligation process with Ligation Kit Ver. 2 (Takara) at 16° C. for about 3 hours. The ligated DNA was introduced into *E. coli* DH5α strain competent cells (TOYOBO) according to the description attached to the above kit. A plasmid DNA was prepared from an ampicillin-resistant colony by alkali method, and the resulting DNA was subjected to sequence analysis. A plasmid with a structure in which the inventive gene was inserted in the Spe I restriction site of pRc/RSV was selected and named plasmid pRc/RSV1ER.

Example 3

Preparation of Reporter Plasmid for the Inventive Reporter Assay

Xenopus genome DNA is purified with Isogen reagent (Nippon Gene) according to the protocol description attached to the reagent. With the purified genome DNA as a template, PCR was performed according to the report by Walker et al. (Nucleic acid Res. (1984) 12, 8611-8626) to amplify a transcriptional control DNA which includes the sequence from the TATA box upstream of the Xenopus vitellogenin gene to the estrogen receptor response element sequence. The amplified DNA is recovered and then treated with Blunting kit (Takara) to have blunt ends (hereinafter the resulting DNA is referred to as ERE DNA).

Two oligonucleotides (an oligonucleotide comprising the nucleotide sequence of SEQ ID NO:15 and an oligonucleotide comprising the nucleotide sequence of SEQ ID NO:16) each having a nucleotide sequence derived from a nucleotide sequence near the TATA box and a leader sequence of mouse metallothionein I gene (Genbank Accession No. J00605) are allowed to anneal to each other to form a double stranded DNA, both ends of which is then phosphorylated with T4 polynucleotide kinase (hereinafter the resulting DNA is referred to as TATA DNA). Firefly luciferase gene-containing plasmid pGL3 (Promega) is digested with restriction enzymes Bgl II and Hind III and then mixed with Bacterial alkaline phosphatase (BAP) and incubated at 65° C. for 1 hour. The incubated solution is then subjected to electrophoresis using a low melting point agarose (AgaroseL, Nippon Gene), and a Bgl II-Hind III fragment DNA containing the pGL3-derived luciferase gene is recovered. About 100 ng of the recovered DNA and 1 µg of TATA DNA are mixed and ligated with T4 ligase to form plasmid pGL3-TATA. The pGL3-TATA is digested with restriction enzyme Sma I and then mixed with BAP and incubated at 65° C. for 1 hour. The incubated solution is then subjected to low melting point agarose gel electrophoresis, and a DNA is recovered from band part of the gel. About 100 ng of the recovered DNA and about 1 µg of ERE DNA are mixed and allowed to react with T4 ligase. From the reaction solution, the DNA is then introduced into *E. coli* DH5α strain competent cells (TOYOBO). From each of several ampicillin-resistant *E. coli* colonies, a plasmid DNA is prepared. Each prepared DNA is digested with restriction enzymes Kpn I and Xho I, and the resulting digest is analyzed by agarose gel electrophoresis. A plasmid with a structure in which one copy of ERE DNA is introduced in the Sma I site of pGL3-TATA is named plasmid pGL3-TATA-ERE, and another plasmid with a structure in which five copies of ERE DNA are introduced in the Sma I site is named plasmid pGL3-TATA-ERE×5.

Example 4

Figure 2:
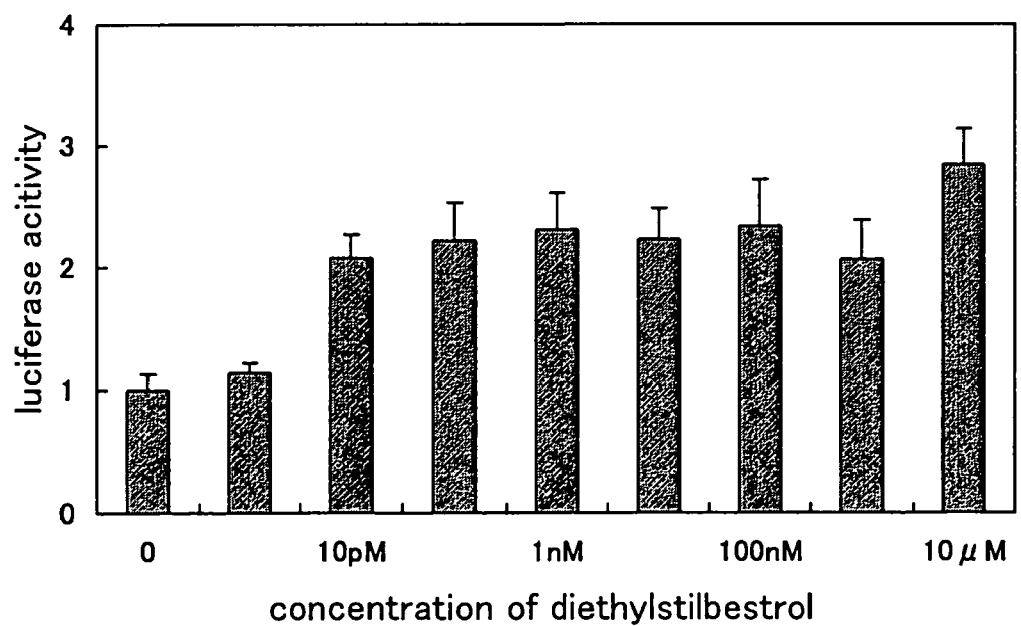
FIG. 2 is a diagram showing a result of determining the ability of diethylstilbestrol (DES) to regulate the estrogen receptor activity by the reporter assay using the inventive gene. The abscissa axis represents the concentration of DES in each assay group. The left end column indicated by O corresponds to an assay group in which DMSO was added at a final concentration of 0.1% in place of the DMSO solution of DES (DES-free group). The ordinate axis represents the luciferase activity value where the luciferase activity value of the DES-free group is normalized as 1.
Figure 3:
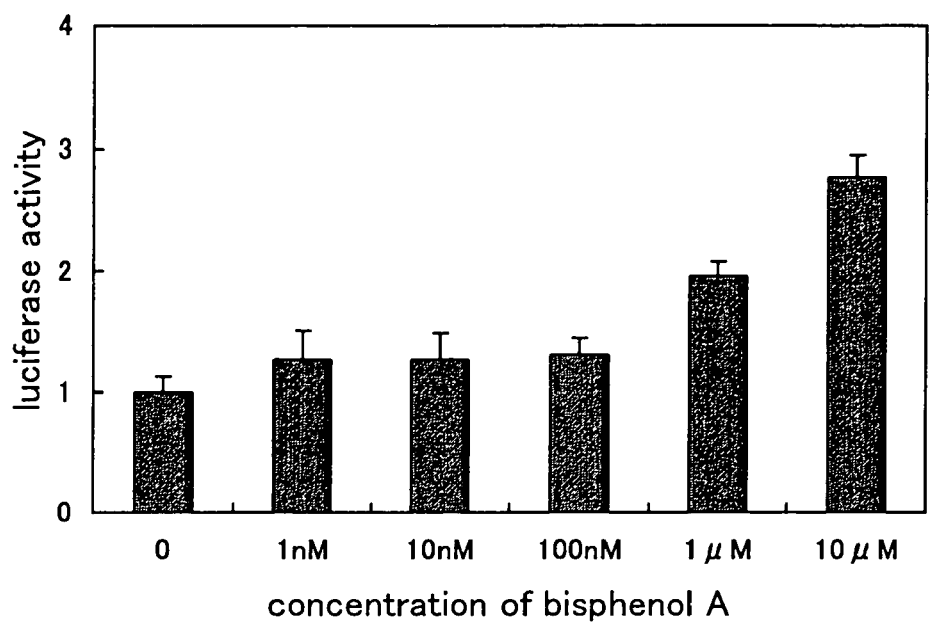
FIG. 3 is a diagram showing a result of determining the ability of bisphenol A to regulate the estrogen receptor activity by the reporter assay using the inventive gene. The abscissa axis represents the concentration of bisphenol A in each assay group. The left end column indicated by O corresponds to an assay group in which DMSO was added at a final concentration of 0.1% in place of the DMSO solution of bisphenol A (bisphenol A-free group). The ordinate axis represents the luciferase activity value where the luciferase activity value of the bisphenol A-free group is normalized as 1.
Figure 4:
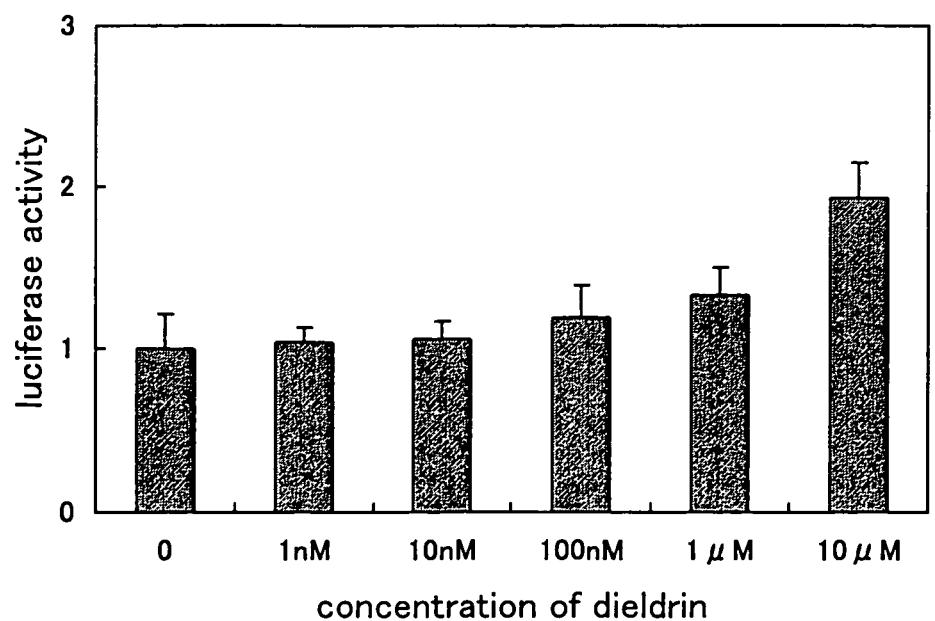
FIG. 4 is a diagram showing a result of determining the ability of dieldrin to regulate the estrogen receptor activity by the reporter assay using the inventive gene. The abscissa axis represents the concentration of dieldrin in each assay group. The left end column indicated by O corresponds to an assay group in which DMSO was added at a final concentration of 0.1% in place of the DMSO solution of dieldrin (dieldrin-free group). The ordinate axis represents the luciferase activity value where the luciferase activity value of the dieldrin-free group is normalized as 1.
Figure 5:
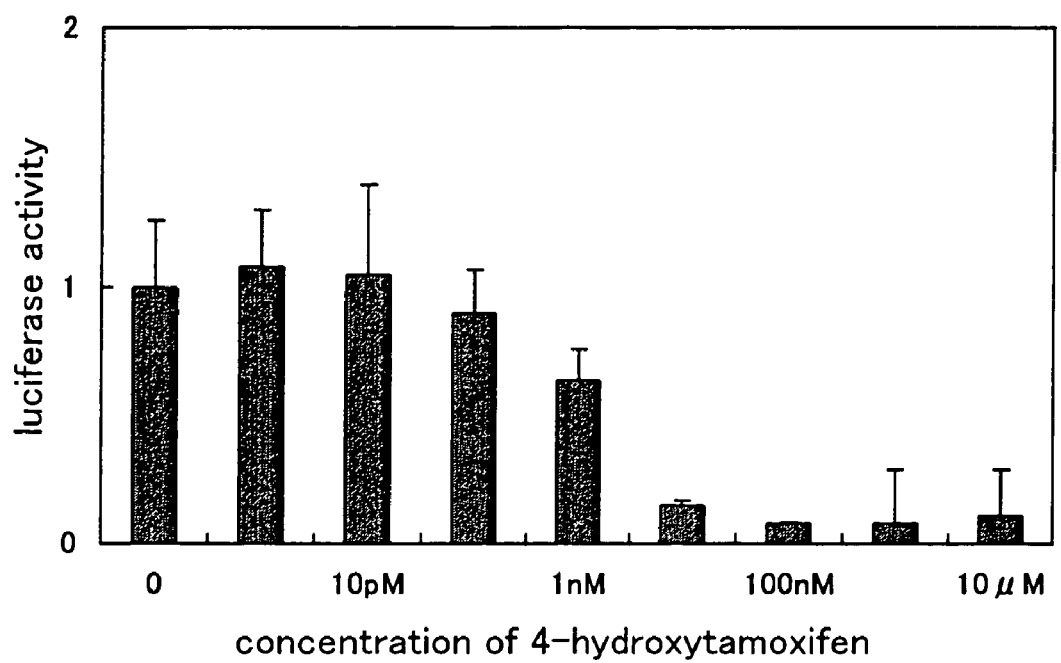
FIG. 5 is a diagram showing a result of determining the ability of 4-hydroxytamoxifen to regulate the estrogen receptor activity by the reporter assay using the inventive gene. The abscissa axis represents the concentration of 4-hydroxytamoxifen allowed to coexist with 100 pM of E2 in each assay group. The left end column indicated by O corresponds to an assay group in which DMSO was added at a final concentration of 0.1% in place of the DMSO solution of 4-hydroxytamoxifen (4-hydroxytamoxifen-free group). The ordinate axis represents the luciferase activity value where the luciferase activity value of the 4-hydroxytamoxifen-free group is normalized as 1.

The Inventive Reporter Assay and Evaluation of the Ability to Regulate the Estrogen Receptor Activity HeLa cells were inoculated on 10 cm plates at a density of about $1 \times 10^6$ cells per plate and cultured in an E-MEM medium containing 10% of charcoal dextran-treated FBS (hereinafter referred to as the FBS-containing E-MEM) under 5% $CO_2$ at 37° C. for 1 day. Lipofectamine (Life Technologies) was used to transfect the resulting cells with 3.5 µg of pRc/RSV1ER and 3.5 µg of pGL3-TATA-ERE×5 according to the protocol. After the transfection, the cells were cultured at 37° C. for 16 hours and then for 3 hours in a replaced medium. The cells were collected and then suspended in the FBS-containing E-MEM medium to be equalized. The equalized cells (suspension) were inoculated on 96-well view plates to which estrogen-like compounds each dissolved in DMSO had each previously been added with different concentrations as follows: E2 (Wako Pure Chemical) at final concentrations of 1 µM to 10 µM, diethylstilbestrol (hereinafter referred to as DES), bisphenol A (Wako Pure Chemical) at final concentrations of 1 nM to 10 µM, dieldrin (GL Sciences) at final concentrations of 1 nM to 10 µM, wherein the final concentration of DMSO is 0.1%. For the purpose of determining the anti-estrogen activity, the equalized cells (suspension) were inoculated on 96-well view plates to which 100 pM of E2 and an anti-estrogen compound at different concentrations (4-hydroxytamoxifen at final concentrations of 1 pM to 10 µM, wherein the final concentration of DMSO is 0.2%) had simultaneously been added similarly. The cells inoculated on the 96-well view plates were cultured at 37° C. for about 40 hours. Cytolytic agent PGC50 (Nippon Gene) 5-fold diluted was added in an amount of 15 µl/well and allowed to stand at room temperature for 30 minutes while sometimes gently shaken, so that the cells were lysed. In Luminometer LB96p equipped with an automatic substrate injector (Berthold), enzyme substrate solution PGL100 (Nippon Gene) was added in an amount of 50 μl/well, and then immediately, the luminescence intensity was measured for 1 second. The results of the measurement of the ability to regulate the estrogen receptor activity are shown in FIGS. 1 to 5.

Example 5

Production of Transformant for the Inventive Reporter Assay 2

Plasmid pUCSV-BSD (purchased from Funakoshi) is digested with BamHI to form a DNA coding for a blasticidin S deaminase gene expression cassette. The prepared DNA and plasmid pGL3-TATA-ERE obtained in Example 3 are digested with BamHI and treated with BAP. The resulting DNA mixture is allowed to react with T4 ligase. The DNA is then introduced from the reaction solution into *E. coli* DH5α competent cells (TOYOBO). An ampicillin-resistant colony is isolated, and a plasmid DNA is prepared from the colony by alkali method. The prepared DNA is digested with restriction enzyme BamHI, and the resulting digest is analyzed by agarose gel electrophoresis. A plasmid with a structure in which the blasticidin S deaminase gene expression cassette is inserted in the BamHI restriction site of plasmid pGL3-TATA-ERE is selected and named plasmid pGL3-TATA-ERE-BSD.

The produced plasmid pGL3-TATA-ERE-BSD DNA and the plasmid pRc/RSV1ER DNA produced in Example 2 are each linearized and then introduced into HeLa cells. The process below is used to form a transformant in which these DNAs are introduced in the host cell chromosome.

Plasmid pGL3-TATA-ERE-BSD DNA and plasmid pRc/RSV1ER DNA are each digested with Sal I. On the other hand, HeLa cells are cultured on plates about 10 cm in diameter (Falcon) with a 10% FBS-containing DMEM medium (Nissui Pharmaceutical) at 37° C. under 5% $CO_2$. About $5 \times 10^5$ cells are cultured for 1 day. The resulting cells are transfected simultaneously with the linearized DNAs by lipofection method using lipofectin (GIBCO). The lipofection method is performed according to the manual description attached to the lipofectin under the following conditions: a treating time of 5 hours, the total amount of the linearized DNAs of 7 μg (each 3.5 μg) per plate, and a lipofectin amount of 20 μl/plate. After the lipofection, the cells are cultured in situ in the 10% FBS-containing DMEM medium for 3 days. The cells are peeled off from the plate by trypsin treatment and then divided into 10 aliquots, inoculated on 10 plates, respectively, and cultured overnight. G418 (Sigma) is then added to the culture at a final concentration of 400 μg/ml. Blasticidin S is also added to the culture at a final concentration of 8 μg/ml, and the cultivation is further carried out. After one week, the medium is replaced with a fresh one containing G418 and blasticidin S each at the same concentration, and the cultivation is further carried out. After a week, the same process is carried out again. After another week, the plates are observed with an inverted microscope, and 30 colonies with a diameter of several mm are each transferred to each well of a 96-well view plate (Berthold) to which a medium has been added to each well in advance, and the cultivation is further carried out. Before grown in a confluent state, the cells are peeled off by trypsin treatment, collected, divided into 3 aliquots, and inoculated on new 3 96-well view plates, respectively. The cells on one plate are subcultured. E2 is added to one of the remaining two plates at a final concentration of 50 nM, and nothing is added to the other plate. The cells on each plate are cultured for 2 days. After the 2 days, each culture supernatant is removed from each plate, and the cells are washed with 200 μl/well of PBS(−) twice. In order to lyse the cells, cytolytic agent PGC50 (Nippon Gene) 5-fold diluted was then added to each view plate in an amount of 20 μl/well and allowed to stand at room temperature for 30 minutes. The plates are each placed in Luminometer LB96p equipped with an automatic enzyme substrate injector (Berthold). While 50 μl of enzyme substrate solution PGL1000 (Nippon Gene) is automatically added to each well, the luciferase activity is measured. When the luciferase activity of the E2-containing test group is at least twice as high as that of the E2-free test group, the transformant cells are selected and collected. Thus, the inventive transformant is prepared, in which the inventive gene is located in the host cell chromosome.

Example 6

The Inventive Reporter Assay 2: Evaluation of the Ability to Regulate the Estrogen Receptor Activity The transformant prepared in Example 5 is inoculated on a 24-well plate at a density of about $4 \times 10^4$ cells/well and cultured under 5% $CO_2$ at 37° C. for 1 day in an E-MEM medium containing 10% of charcoal dextran-treated FBS, 400 μg/ml of G418, and 8 μg/ml of blasticidin S (hereinafter referred to as the FBS and antibiotic-containing E-MEM medium). A test substance DMSO (Wako Pure Chemical) solution is added to the FBS and antibiotic-containing E-MEM medium in different amounts so as to provide final test substance concentrations of 1 nM to 50 μM. Alternatively, DMSO is added to the FBS and antibiotic-containing E-MEM medium in the same amount as that of above each test substance solution. Alternatively, a DMSO solution of. E2 is added to the FBS and antibiotic-containing E-MEM medium so as to provide an E2 final concentration of 1 μM. The above cell culture supernatant is replaced with each of the above resulting mediums. The cell culture is held in a $CO_2$ incubator for 24 hours, and then the culture supernatant is removed from the plate. While attention is paid not to peel off the adhering cells from the plate, the cells are washed with 1 ml/well of PBS(−) twice. For the purpose of lysing the cells, cytolytic agent PGC50 (Nippon Gene) 5-fold diluted is added to the plate in an amount of 50 μl/well and allowed to stand at room temperature for 30 minutes while sometimes gently shaken. The resulting lysis solution is placed on a 96-well white sample plate (Berthold) in an amount of 10 μl/well. In Luminometer LB96p equipped with an automatic substrate injector (Berthold), enzyme substrate solution PGL100 (Nippon Gene) is added to the plate in an amount of 50 μl/well, and immediately, the luminescence intensity from each well is measured for 5 seconds.

This reporter assay can also find a substance having the ability to regulate the estrogen receptor activity.

Example 7

Production of Chimera Gene 1-Containing Vector in the Production of the Inventive Protein Complex Gene Introduced Transformant (Part 1)

PCR is performed using plasmid pRc/RSV1ER as a template and using an oligonucleotide comprising the nucleotide sequence of SEQ ID NO:17 and an oligonucleotide comprising the nucleotide sequence of SEQ ID NO:18 as primers (the PCR reaction conditions: 25 cycles of 94° C. for 1 minute, 55° C. for 1 minute, and 74° C. for 1.5 minutes). The PCR amplifies a DNA including the nucleotide sequence from nucleotide 763 to 1746 of the SEQ ID NO:2 sequence (the DNA which includes a nucleotide sequence coding for the ligand binding domain of the estrogen receptor out of the inventive gene nucleotide sequence and excludes the nucleotide sequence coding for the amino acid sequence of element (X) from group II).

The amplified DNA is treated with chloroform/phenol and then precipitated with ethanol. The precipitate is centrifugally washed with 70% ethanol and then dried. The DNA is dissolved with TE added and then digested with restriction enzymes EcoRI and SalI at 37° C. for about 5 hours. The digest is subjected to 1% agarose gel electrophoresis and separated. About 1 kbp DNA-containing part of the gel is cut out, and the DNA is recovered from the part using GENECLEAN (Funakoshi). Vector pGBT9 (Clontech) (about 50 ng), for the production of the chimera protein of GAL4 protein and the DNA binding region, is digested with EcoRI and SalI and then subjected to 1% agarose gel electrophoresis. The EcoRI and SalI-digested vector DNA is then recovered using GENECLEAN (Funakoshi). The recovered vector DNA and about 10 ng of the above recovered DNA are mixed with each other. A ligation solution (Ligation Kit, Takara) is added to the mixture in the same volume and incubated at 16° C. for about 5 hours. The resulting mixture is then introduced into competent DH5α cells (TOYOBO) according to the process description attached to the kit. An ampicillin-resistant colony is isolated, and a plasmid DNA is prepared from the colony by alkali method. The nucleotide sequence of the prepared plasmid DNA is confirmed and then named pGBT9-1ERLID. This plasmid can be applied to the two-hybrid assay using the budding yeast as the host cell.

Example 8

Production of Chimera Gene 2-Containing Vector in the Production of the Inventive Protein Complex Gene Introduced Transformant (Part 2)

A cDNA is produced using a human brain-derived mRNA (Clontech) and RT-PCR kit (Takara) in accordance with the protocol attached to the products. PCR is performed using the produced cDNA as a template and using an oligonucleotide comprising the nucleotide sequence of SEQ ID NO:19 and an oligonucleotide comprising the nucleotide sequence of SEQ ID NO:20 as primers (the PCR reaction conditions: 30 cycles of 94° C. for 1 minute, 55° C. for 1 minute, and 72° C. for 2.5 minutes). The PCR amplifies a DNA coding for the amino acid sequence between amino acids 624 and 1287 from the amino terminal end of transcription coupling factor TIF2. The amplified DNA is treated with chloroform/phenol and then precipitated with ethanol. The precipitate is centrifugally washed with 70% ethanol and then dried. The DNA is dissolved with TE added and then digested with restriction enzymes EcoRI and BglII at 37° C. for 5 hours. The digest is subjected to 1% agarose gel electrophoresis and separated. About 2.0 kbp DNA-containing part of the gel is cut out, and the DNA is recovered from the part using GENECLEAN (Funakoshi). Vector pGAD424 (Clontech) (about 50 ng), for the production of the chimera protein of GAL4 protein and the transcription activating domain, is digested with EcoRI and BamHI and then subjected to 1% agarose gel electrophoresis. The EcoRI and BamHI-digested vector DNA is then recovered using GENECLEAN (Funakoshi). The recovered vector DNA and about 10 ng of the above-recovered DNA are mixed with each other. A ligation solution (Ligation Kit, Takara) is added to the mixture in the same volume and incubated at 16° C. for about 1 hour. The resulting mixture is then introduced into E. coli DH5α competent cells (TOYOBO) according to the process description attached to the kit. An ampicillin-resistant colony is isolated, and a plasmid DNA is prepared from the colony by alkali method. The nucleotide sequence of the prepared plasmid DNA is confirmed and then named pGAD424-TIF2RID. This plasmid can be applied to the two-hybrid assay using the budding yeast as the host cell.

Example 9

Preparation of the Inventive Two-Hybrid System

Yeast Y190 (Clontech) is shake-cultured in YPD medium at 30° C. overnight according to the manual of Matchmaker Two-Hybrid System (Clontech). The cultured yeast cells are collected and then transfected with pGBT9-1ERLID obtained in Example 7 and pGAD424-TIF2RID obtained in Example 3 using Yeastmaker yeast transformation system (Clontech). The two plasmid-introduced yeast cells are inoculated on a tryptophan or leucine-free SD nutrient agar and cultured at 30° C. for about 2 days. After the culture is completed, a grown colony is selected, applied again on the tryptophan or leucine-free SD nutrient agar, and cultured at 30° C. for about 2 days. The cultured yeast is used for the two-hybrid system.

Example 10

Evaluation of the Ability of Substances to Regulate the Estrogen Receptor Activity Using the Inventive Two-Hybrid System Part of the cultured yeast cells obtained in Example 9 are seeded in 1 ml of a tryptophan or leucine-free SD medium and shake-cultured at 30° C. overnight. The resulting liquid culture is diluted with the tryptophan or leucine-free SD medium so as to provide an absorbance of 0.015 at 595 nm. To each well of a 96-well deep well plate are added 250 µl of the tryptophan or leucine-free SD medium, a DMSO solution of an estrogen-like compound (prepared with a final DMSO concentration of 1%), and 10 µl of the diluted liquid culture and shake-cultured at 30° C. for 4 hours. From each well, 10 µl of the liquid culture is then sampled, and 100 µl of a luminescence reaction solution (Gal-Screen, Tropix) for the measurement of β-galactosidase activity is added to each sample and then incubated at room temperature for about 1 hour. The luminescence intensity from each well is then measured with Luminometer LB96p (Berthold).

Example 11

Production of the Inventive Gene-Containing Viral Particles and Virus Vector

At 37° C., 2 µg of the inventive vector pRC/RSV-1ER DNA prepared in Example 2 is digested with 10U of restriction enzyme SpeI for 1 hour. The digest is subjected to low melting point agarose gel electrophoresis, and a DNA with a length of about 1.8 kbp is recovered. The DNA is made blunt with a blunting kit (Takara) according to the manual. On the other hand, 2 µg of pVL1392 vector DNA is digested with 10 U of restriction enzyme SmaI and treated with 10 U of alkaline phosphatase at 65° C. for 1 hour and then subjected to low melting point agarose gel electrophoresis, and the DNA is recovered. About 100 ng of the about 1.8 bp DNA prepared from pRC/RSV-1ER as described above and 5 U of T4 Ligase are added to 100 ng of the recovered pVL1392 vector DNA. The resulting mixture is then incubated at 16° C. for 3 hours. The mixture is then introduced into *E. coli* DH5α strain competent cells (TOYOBO) according to the process description. Ampicillin-resistant colonies are isolated, and plasmid DNAs are prepared from the colonies by alkali method. About 1 μg of each plasmid DNA is digested with 10 U of restriction enzymes XbaI at 37° C. for 1 hour. The digest is analyzed by agarose electrophoresis using agarose S (Nippon Gene). A plasmid which provides an about 1.4 kbp band is named transfer vector pVL1392-1ER. To a 75 cm$^2$ T-flask (Falcon) are added 1×10$^6$ of Sf21 cells (available from ATCC), and cultured at 27° C. overnight using a Grace's medium containing 10% FBS and 2% Yeastlate (hereinafter referred to as the FBS-containing Grace medium). To 100 μl of the Grace 's medium are added 10 μg of the produced transfer vector pVL1392-1ER DNA and 20 ng of linearized viral genome DNA Baculo gold (Pharmingen). After 10 μl of lipofectin (GIBCO) 2-fold diluted with water is further added to the medium, the medium (the lipofectin-DNA mixture solution) is allowed to stand at room temperature for 30 minutes. After the overnight culture, the supernatant is removed from the Sf21 cell culture. The cells are washed with a small amount of a serum-free Grace's medium. To the cells is then added 5 ml of the same medium. The whole amount of the lipofectin-DNA mixture solution is then added to the cells, which is incubated 27° C. for 3 hours. The cells are then washed with the FBS-containing Grace medium. To the cells is also added 20 ml of the FBS-containing Grace medium, and the cells are cultured at 27° C. for 5 days. Day five of the culture, the supernatant is collected in a 50 ml centrifuge tube and centrifuged at 5000×g for 15 minutes to have cell debris precipitated, and then the centrifuged supernatant is collected. The whole amount of the collected supernatant is centrifuged at 100,000×g for 24 hours to give precipitated viral particles that contain the inventive gene. The precipitate is suspended in 100 μl of TE. An equivalent amount of TE-saturated phenol is added thereto and gently mixed at room temperature for 24 hours. After the mixture is centrifuged at 10,000×g for 10 minutes, a water layer is collected. An equivalent amount of chloroform is added to the collected water layer and gently mixed for 10 minutes. The mixture is again centrifuged at 10,000×g for 10 minutes, and then the water layer is collected. To the collected water layer are added NaCl at a final concentration of 0.2 M and a 2.5-fold amount of ethanol, and a viral vector DNA that contains the inventive gene is precipitated and collected.

Example 12

Production of the Inventive Transformant and Production of the Inventive Estrogen Receptor To each of ten 75 cm$^2$ T-flasks (Falcon) is added 1×10$^6$ of Sf21 cells (available from ATCC), and cultured in the FBS-containing Grace medium at 27° C. In each flask, 10 μl/flask of the culture supernatant, which is prepared in Example 11 and contains the inventive gene-containing viral particles, is added to the cells, which are cultured in situ for 4 days. The culture supernatant is harvested from each flask and then added to Sf21 cells, which are similarly cultured in each of ten 75 cm$^2$ T-flasks (Falcon), in an amount of 1 ml per flask. The cells are cultured for 60 hours in each flask and then suspended by pipetting and harvested from each flask. The resulting cell suspension is centrifuged at 5,000×g for 15 minutes to have the cells precipitated. The precipitate is suspended in a buffer comprising 20 mM HEPES pH 7, 1 mM EDTA, 1 mM DTT, and 0.5 mM PMSF, and then the suspension is homogenized with 30 up-and-down strokes in a Dounce homogenizer to form a cell homogenate. The homogenate is centrifuged at 30,000×g for 1 hour, and the supernatant fraction is collected to give a fraction that contains the inventive estrogen receptor.

Example 13

The Inventive Receptor Binding Assay

A binding reaction buffer is prepared to have a final composition of 20 mM HEPES-KOH pH 7.9, 10 mM sodium molybdate, 1 mM DTT, 0.5 mM EDTA, and 0.5 mM PMSF. The reaction solution has a total volume of 100 μl. To the binding reaction buffer are added a 10 μg protein equivalent of the inventive estrogen receptor-containing fraction prepared in Example 12 and tritium-labeled E2 (which may hereinafter be referred to as the labeled E2) at a content of 1 pM to 100 nM. In the group for determining nonspecific binding, unlabeled E2 is further added at a final concentration of 10 μM to form a reaction solution.

The binding reaction is carried out as follows. After the reaction solution is held on ice for 15 hours, 100 μl of a charcoal dextran liquid (composition: 10 mM Tris-HCl, 0.2% acid-washed active carbon (NoritA, Nacalai Tesque), and 0.005% Pharmacia Dextran T70) is added, and the reaction mixture is allowed to stand on ice for 10 minutes. The reaction mixture is centrifuged at 1,000×g for 10 minutes in a low-speed centrifuge to have the active carbon precipitated, and then 100 μl of the supernatant is sampled. The radioactivity of the sampled supernatant is measured using a liquid scintillation counter. Based on the measured value, the amount of the labeled E2 in the supernatant is determined, which corresponds to the amount of the labeled E2 bound to the estrogen receptor (the amount of the bound form of the labeled ligand). In the test group to which only the labeled E2 is added, the amount of the bound form of the labeled ligand corresponds to the total amount of the labeled E2 bound to the estrogen receptor (the total binding amount). In the test group to which the labeled E2 and unlabeled E2 are added, the amount of the bound form of the labeled ligand corresponds to the amount of the labeled E2 nonspecifically bound to the estrogen receptor (the nonspecific binding amount). As for each of the test groups to which the labeled E2 is added at different concentrations, respectively, the nonspecific binding amount is subtracted from the total binding amount to produce the amount of the labeled ligand specifically bound to the estrogen receptor (the specific binding amount) in each group. Thereafter, the value of (the concentration of the labeled ligand specifically bound)/(the concentration of the free form of the labeled ligand) is plotted against the Y-axis, and the concentration of the labeled ligand specifically bound is plotted against the X-axis. The Scatchard analysis is performed to produce a Kd value of the inventive estrogen receptor with respect to E2.

In order to determine the affinity of a test substance for the inventive estrogen receptor, the test substance is added at a final concentration of about 1% to the binding assay reaction solution, which contains about 1 nM of the labeled E2 similarly to the above. In the test substance-free test group, the same amount of solvent is added to the reaction solution in place of the test substance. When the addition of the test substance reduces the amount of the labeled E2 bound to the estrogen receptor, the test substance is determined as an estrogen receptor binding substance.

INDUSTRIAL APPLICABILITY

According to the present invention, the estrogen receptor gene and the like can be applied to assay systems for evaluating the ability of chemical substances to regulate the estrogen receptor activity.

Free Text in Sequence Listing
SEQ ID NO:3
  Designed oligonucleotide primer for PCR
SEQ ID NO:4
  Designed oligonucleotide primer for PCR
SEQ ID NO:5
  Designed oligonucleotide primer for PCR
SEQ ID NO:6
  Designed oligonucleotide primer for PCR
SEQ ID NO:7
  Designed oligonucleotide primer for PCR
SEQ ID NO:8
  Designed oligonucleotide primer for PCR
SEQ ID NO:9
  Designed oligonucleotide primer for PCR
SEQ ID NO:10
  Designed oligonucleotide primer for PCR
SEQ ID NO:11
  Designed oligonucleotide primer for PCR
SEQ ID NO:12
  Designed oligonucleotide primer for PCR
SEQ ID NO:13
  Designed oligonucleotide primer for PCR
SEQ ID NO:14
  Designed oligonucleotide to synthesize promoter DNA
SEQ ID NO:15
  Designed oligonucleotide to synthesize promoter DNA
SEQ ID NO:16
  Designed oligonucleotide primer for PCR
SEQ ID NO:17
  Designed oligonucleotide primer for PCR
SEQ ID NO:18
  Designed oligonucleotide primer for PCR
SEQ ID NO:19
  Designed oligonucleotide primer for PCR
SEQ ID NO:20
  Designed oligonucleotide primer for PCR
SEQ ID NO:21
  Designed oligonucleotide primer for PCR
SEQ ID NO:22
  Consensus sequence to be bound by Gal protein
SEQ ID NO:23
  Consensus sequence to be bound by Lex protein
SEQ ID NO:24
  Consensus sequence to be bound by Lac I receptor protein
SEQ ID NO:25
  Consensus sequence to be bound by Tetracyclin receptor protein
SEQ ID NO:26
  Consensus sequence to be bound by ZFHD-1
SEQ ID NO:27
  Consensus sequence to be bound by Estrogen receptor

The invention claimed is:

1. An isolated nucleic acid encoding an estrogen receptor, wherein the nucleic acid comprises a nucleotide sequence coding for any one of the following amino acid sequences:
   (a) the amino acid sequence of SEQ ID NO:1,
   (b) an amino acid sequence of a protein having an estrogen receptor activity, the amino acid sequence having at least 85% sequence identity with the amino acid sequence of SEQ ID NO:1,
   (c) an amino acid sequence encoded by the nucleotide sequence of SEQ ID NO:2, or
   (d) an amino acid sequence of a protein having an estrogen receptor activity, the amino acid sequence being encoded by a nucleotide sequence having at least 85% sequence identity with a DNA having the nucleotide sequence of SEQ ID NO:2.

2. An isolated nucleic acid encoding an estrogen receptor, wherein the nucleic acid comprises the nucleotide sequence of SEQ ID NO:2.

3. A vector comprising the nucleic acid encoding the estrogen receptor according to claim 1.

4. The vector according to claim 3 further comprising a promoter operably linked to the nucleic acid encoding estrogen receptor.

5. A method for producing a vector comprising incorporating the nucleic acid encoding the estrogen receptor according to claim 1 into a vector replicable in a host cell.

6. A transformant being formed by introducing a vector comprising the nucleic acid encoding the estrogen receptor according to claim 1 in a host cell.

7. The transformant according to claim 6, wherein the nucleic acid encoding the estrogen receptor is located in a chromosome of the host cell.

8. The transformant according to claim 6, wherein the host cell is an animal cell or a yeast cell.

9. A method for producing a transformant, comprising introducing a vector comprising the nucleic acid encoding the estrogen receptor according to claim 1 into a host cell.

10. A method for producing an estrogen receptor, comprising culturing the transformant according to claim 6 under conditions by which the estrogen receptor is produced by the transformant.

11. An isolated DNA comprising a partial nucleotide sequence of the nucleic acid encoding the estrogen receptor according to claim 1.

12. The DNA according to claim 11, wherein the partial nucleotide sequence is a nucleotide sequence coding for an amino acid sequence of a ligand binding domain of the estrogen receptor.

13. A transformant, being formed by introducing, into a host cell, one or more vectors comprising:
   (1) a first nucleic acid having one of the elements from group i below (either a or b) and one of the elements from group ii below (either x or y);
   (2) a second nucleic acid having the other of the elements from group i below (either b or a) and the other of the elements from group ii below (either y or x); and
   (3) a third nucleic acid having element iii below, group i consisting of the following elements:
      (a) a DNA having a nucleotide sequence coding for an amino acid sequence of an estrogen receptor binding region of a transcription coupling factor capable of binding, under the control of a ligand, to a transcription coupling factor binding region of an estrogen receptor having an amino acid sequence encoded by the nucleotide sequence of the nucleic acid encoding the estrogen receptor according to claim 1; and
      (b) a DNA having a nucleotide sequence coding for an amino acid sequence of a transcription coupling factor binding region of an estrogen receptor, wherein the transcription coupling factor binding region of the estrogen receptor has an amino acid sequence at least 85% identical to the amino acid sequence encoded by the nucleotide sequence of from nucleotide 877 to nucleotide 1623 of SEQ ID NO:2, and wherein the transcription coupling factor binding region of the estrogen receptor is capable of binding, under the control of a ligand, to the estrogen receptor binding region of a transcription coupling factor according to group i (a);
   group ii consisting of the following elements:
      (x) a DNA having a nucleotide sequence coding for an amino acid sequence of a DNA binding region of a transcriptional control factor operable in a host cell; and
      (y) a DNA having a nucleotide sequence coding for an amino acid sequence of a transcription activating domain of a transcriptional control factor operable in a host cell; and
   element iii comprising:
      a DNA to which a DNA binding region having an amino acid sequence encoded by the nucleotide sequence of element (x) from group ii is capable of binding; and
      a DNA having a reporter gene linked downstream of a promoter which can be activated by a transcription activating domain having an amino acid sequence encoded by the nucleotide sequence of element (y) from group ii.

14. The transformant according to claim 13, wherein element (x) from group ii is a DNA having a nucleotide sequence coding for an amino acid sequence of a protein which is capable of binding to a DNA comprising any one of the following nucleotide sequences:
   (1) a Gal protein-binding DNA nucleotide sequence (5'-CGGACAACTGTTGACCCG-3'(SEQ ID NO:22)),
   (2) a Lex protein-binding DNA nucleotide sequence (5'-TACTGTATGTACATACAGTA-3' (SEQ ID NO:23),
   (3) a Lac I receptor protein-binding DNA nucleotide sequence (5'-GAATTGTGAGCGCGCACAATTc-3' (SEQ ID NO:24),
   (4) a tetracycline receptor protein-binding DNA nucleotide sequence (5'-TCGAGTTTACCACTCCCTATCAGT-GATAGAGAAAAGTGAAAG3' (SEQ ID NO:25),
   (5) a ZFHD-1 protein binding DNA nucleotide sequence (5'-TAATGATGGGCG-3' (SEQ ID NO:26)), and
   (6) an estrogen response nucleotide sequence (5'-GGT-CANNNTGACC-3' (SEQ ID NO:27)).

15. The transformant according to claim 13, wherein element (y) from group ii is derived from a DNA having a nucleotide sequence coding for the amino acid sequence of any one of the following proteins:

(1) Gal protein,
(2) Lex protein,
(3) Lac I receptor protein,
(4) a tetracycline receptor protein,
(5) ZFHD-1 protein,
(6) B42 protein, and
(7) a transcription coupling factor capable of binding, under the control of a ligand, to a transcription coupling factor binding region of an estrogen receptor having an amino acid sequence encoded by the nucleotide sequence of the estrogen receptor gene according to claim 1.

16. The transformant according to claim 13, wherein element (b) from group i comprises a DNA having a nucleotide sequence coding for an amino acid sequence of a domain to which the ligand is capable of binding.

* * * * *

UNITED STATES PATENT AND TRADEMARK OFFICE
CERTIFICATE OF CORRECTION

PATENT NO. : 7,419,800 B2
APPLICATION NO. : 10/451768
DATED : September 2, 2008
INVENTOR(S) : Kayo Sumida It is certified that error appears in the above-identified patent and that said Letters Patent is hereby corrected as shown below:

Column 49, lines 1-12 and Col. 50 lines 1-6

Claim 15 should read:

-- 15. The transformant according to claim 21, wherein element (y) from group ii is derived from a DNA having a nucleotide sequence coding for the amino acid sequence of any one of the following proteins:
    (1) Gal protein,
    (2) Lex protein,
    (3) Lac I receptor protein,
    (4) a tetracycline receptor protein,
    (5) ZFHD-1 protein,
    (6) B42 protein, and
    (7) a transcription coupling factor capable of binding, under the control of a ligand, to a transcription coupling factor binding region of an estrogen receptor having an amino acid sequence encoded by a nucleic acid encoding the estrogen receptor, wherein the nucleic acid comprises a nucleotide sequence coding for any one of the following amino acid sequences:
    (a) the amino acid sequence of SEQ ID NO:1,
    (b) an amino acid sequence of a protein having an estrogen receptor activity, the amino acid sequence having at least 85% sequence identity with the amino acid sequence of SEQ ID NO:1,
    (c) an amino acid sequence encoded by the nucleotide sequence of SEQ ID NO:2, or

UNITED STATES PATENT AND TRADEMARK OFFICE
CERTIFICATE OF CORRECTION

PATENT NO. : 7,419,800 B2
APPLICATION NO. : 10/451768
DATED : September 2, 2008
INVENTOR(S) : Kayo Sumida It is certified that error appears in the above-identified patent and that said Letters Patent is hereby corrected as shown below:

(d) an amino acid sequence of a protein having an estrogen receptor activity, the amino acid sequence being encoded by a nucleotide sequence having at least 85% sequence identity with a DNA having the nucleotide sequence of SEQ ID NO:2. --

Signed and Sealed this

Eleventh Day of November, 2008

JON W. DUDAS
*Director of the United States Patent and Trademark Office*

```
                         SEQUENCE LISTING

<160> NUMBER OF SEQ ID NOS: 27

<210> SEQ ID NO 1
<211> LENGTH: 581
<212> TYPE: PRT
<213> ORGANISM: Cnemidophorus uniparens

<400> SEQUENCE: 1

Met Thr Met Thr Leu His Thr Lys Thr Ser Gly Val Ala Leu Leu His
 1               5                  10                  15

Gln Ile Gln Gly Ser Glu Leu Glu Pro Leu Asn Arg Pro Gln Leu Lys
             20                  25                  30

Ile Pro Leu Glu Arg Pro Ile Ser Glu Met Tyr Val Asp Ser Asn Lys
         35                  40                  45

Thr Gly Val Phe Asn Tyr Pro Glu Gly Ala Thr Tyr Asp Phe Ser Thr
     50                  55                  60

Ala Ala Pro Val Tyr Ser Ser Ala Ser Leu Ser Tyr Ala Ser Thr Asn
 65                  70                  75                  80

Glu Ser Phe Gly Ser Gly Asn Leu Gly Gly Leu His Ser Leu Asn Asn
                 85                  90                  95

Val Pro Pro Ser Pro Val Val Phe Leu Gln Thr Ala Pro Gln Leu Ser
            100                 105                 110

Pro Phe Ile His His His Asn Gln Gln Val Pro Tyr Tyr Leu Glu Asn
        115                 120                 125

Glu Pro Ser Ser Ser Ala Met Arg Glu Ala Phe Pro Thr Ala Phe Tyr
    130                 135                 140

Arg Pro Gly Ser Glu Asn Arg His His Gly Gly Arg Ala Ser Asn Ser
145                 150                 155                 160
```

```
Glu Lys Gly Ser Leu Ser Met Glu Ser Thr Lys Glu Thr Arg Tyr Cys
                165                 170                 175
Ala Val Cys Asn Asp Tyr Ala Ser Gly Tyr His Tyr Gly Val Trp Ser
            180                 185                 190
Cys Glu Gly Cys Lys Ala Phe Phe Lys Arg Ser Ile Gln Gly His Asn
        195                 200                 205
Asp Tyr Met Cys Pro Ala Thr Asn Gln Cys Thr Ile Asp Lys Asn Arg
    210                 215                 220
Arg Lys Ser Cys Gln Ala Cys Arg Leu Arg Lys Cys Tyr Glu Val Gly
225                 230                 235                 240
Met Met Lys Gly Gly Ile Arg Lys Asp Arg Arg Gly Gly Arg Met Leu
                245                 250                 255
Lys His Lys Arg Gln Arg Asp Glu Leu Asp Gly Arg Asn Ala Val Ala
            260                 265                 270
Val Thr Glu Ala Arg Asn Thr Thr Leu Trp Pro Ser Pro Leu Met Ile
        275                 280                 285
Lys His Ser Lys Lys Asn Ser Pro Ala Leu Ser Leu Thr Ala Glu Gln
    290                 295                 300
Met Val Ser Ala Leu Leu Asp Ala Glu Pro Pro Ile Val Tyr Ser Glu
305                 310                 315                 320
Tyr Asp Pro Ser Ser Pro Phe Ser Glu Ala Ser Val Met Thr Leu Leu
                325                 330                 335
Thr Asn Leu Ala Asp Arg Glu Leu Val His Met Ile Thr Trp Ala Lys
            340                 345                 350
Arg Val Pro Gly Phe Val Asp Leu Ala Leu His Asp Gln Val His Leu
        355                 360                 365
Leu Glu Cys Ala Trp Leu Glu Ile Leu Met Ile Gly Leu Ile Trp Arg
    370                 375                 380
Ser Leu Glu His Pro Gly Lys Leu Leu Phe Ala Pro Asn Leu Leu Leu
385                 390                 395                 400
Asp Arg Ser Gln Gly Met Cys Val Glu Gly Phe Val Glu Ile Phe Asp
                405                 410                 415
Met Leu Leu Ala Thr Ser Ser Arg Phe Arg Met Met Asn Ile Gln Gly
            420                 425                 430
Glu Glu Phe Val Cys Leu Lys Ser Ile Ile Leu Leu Asn Ser Gly Ile
        435                 440                 445
Tyr Thr Phe Leu Ser Ser Thr Leu Arg Ser Leu Glu Glu Lys Glu His
    450                 455                 460
Ile His Arg Val Leu Asp Lys Ile Thr Asp Thr Leu Thr His Leu Met
465                 470                 475                 480
Ala Lys Ser Gly Leu Ser Leu Gln Gln Gln His Arg Arg Leu Ala Gln
                485                 490                 495
Leu Leu Leu Met Leu Ser His Ile Arg His Met Ser Asn Lys Gly Met
            500                 505                 510
Glu His Leu Tyr Asn Met Lys Cys Lys Asn Val Val Pro Leu Tyr Asp
        515                 520                 525
Leu Leu Leu Glu Met Leu Asp Ala His Arg Leu His Glu Arg Arg Thr
    530                 535                 540
Pro Thr Ser Glu Gln Ala Met Asn Gln Leu Thr Asn Ala Ser Thr Ser
545                 550                 555                 560
Val His Ser Leu Pro Pro Cys Tyr Val Asn Lys Arg Glu Glu Asn
                565                 570                 575
```

```
       Glu Gln Glu Ala Val
               580

<210> SEQ ID NO 2
<211> LENGTH: 1746
<212> TYPE: DNA
<213> ORGANISM: Cnemidophorus uniparens
<220> FEATURE:
<221> NAME/KEY: CDS
<222> LOCATION: (1)...(1746)

<400> SEQUENCE: 2 atg acc atg acc ctt cac aca aaa acc tct ggt gtt gcc tta ttg cac        48
Met Thr Met Thr Leu His Thr Lys Thr Ser Gly Val Ala Leu Leu His
  1               5                  10                  15 cag ata caa ggc agt gag cta gag cct ctg aac aga cct cag ctg aaa        96
Gln Ile Gln Gly Ser Glu Leu Glu Pro Leu Asn Arg Pro Gln Leu Lys
             20                  25                  30 att cct ctg gaa cga ccg atc agt gaa atg tat gtg gat agt aat aag       144
Ile Pro Leu Glu Arg Pro Ile Ser Glu Met Tyr Val Asp Ser Asn Lys
         35                  40                  45 act ggg gtt ttc aac tac cca gaa ggt gcc act tat gat ttt tcc act       192
Thr Gly Val Phe Asn Tyr Pro Glu Gly Ala Thr Tyr Asp Phe Ser Thr
     50                  55                  60 gct gct cca gtg tac agc tca gct agc ctc agt tat gcc tct aca aat       240
Ala Ala Pro Val Tyr Ser Ser Ala Ser Leu Ser Tyr Ala Ser Thr Asn
 65                  70                  75                  80 gaa tcg ttt ggg tcc ggt aac ctg gga gga ctt cat tct ctg aat aat       288
Glu Ser Phe Gly Ser Gly Asn Leu Gly Gly Leu His Ser Leu Asn Asn
                 85                  90                  95 gtt cct cca agc cct gtt gtg ttt tta cag aca gca cca cag ctt tca       336
Val Pro Pro Ser Pro Val Val Phe Leu Gln Thr Ala Pro Gln Leu Ser
            100                 105                 110 cct ttt att cat cac cat aac cag cag gta cct tac tac ctt gag aat       384
Pro Phe Ile His His His Asn Gln Gln Val Pro Tyr Tyr Leu Glu Asn
        115                 120                 125 gaa cca agc agc tct gca atg aga gaa gcc ttt ccc aca gcc ttc tac       432
Glu Pro Ser Ser Ser Ala Met Arg Glu Ala Phe Pro Thr Ala Phe Tyr
    130                 135                 140 agg cca ggc tca gaa aac aga cac cat ggt ggc agg gcc agc aac agt       480
Arg Pro Gly Ser Glu Asn Arg His His Gly Gly Arg Ala Ser Asn Ser
145                 150                 155                 160 gaa aag gga agt ctt tcc atg gaa tct acc aag gag acc cgg tat tgt       528
Glu Lys Gly Ser Leu Ser Met Glu Ser Thr Lys Glu Thr Arg Tyr Cys
                165                 170                 175 gct gtg tgc aat gac tac gct tca ggc tat cat tat ggt gtt tgg tcc       576
Ala Val Cys Asn Asp Tyr Ala Ser Gly Tyr His Tyr Gly Val Trp Ser
            180                 185                 190 tgc gag ggc tgc aaa gcc ttc ttc aaa aga agt att caa ggt cac aat       624
Cys Glu Gly Cys Lys Ala Phe Phe Lys Arg Ser Ile Gln Gly His Asn
        195                 200                 205 gac tac atg tgt cct gct acc aat cag tgc aca att gac aag aac agg       672
Asp Tyr Met Cys Pro Ala Thr Asn Gln Cys Thr Ile Asp Lys Asn Arg
    210                 215                 220 aga aag agc tgc cag gct tgt agg ctc cga aaa tgc tat gaa gtt gga       720
Arg Lys Ser Cys Gln Ala Cys Arg Leu Arg Lys Cys Tyr Glu Val Gly
225                 230                 235                 240 atg atg aaa ggt ggg att cga aaa gac cgc aga ggt ggc cgt atg ctg       768
Met Met Lys Gly Gly Ile Arg Lys Asp Arg Arg Gly Gly Arg Met Leu
                245                 250                 255 aaa cac aag cga caa aga gac gag ctt gat ggc agg aat gca gtg gct       816
```

```
                Lys His Lys Arg Gln Arg Asp Glu Leu Asp Gly Arg Asn Ala Val Ala
                                260                 265                 270 gta act gag gca aga aac acc act cta tgg cca agt ccc ctg atg att          864
Val Thr Glu Ala Arg Asn Thr Thr Leu Trp Pro Ser Pro Leu Met Ile
            275                 280                 285 aaa cat agc aag aag aac agt cca gcc ctg tct ctg act gca gag cag          912
Lys His Ser Lys Lys Asn Ser Pro Ala Leu Ser Leu Thr Ala Glu Gln
290                 295                 300 atg gtc agt gcc ttg tta gat gct gag cct cct att gtc tat tca gaa          960
Met Val Ser Ala Leu Leu Asp Ala Glu Pro Pro Ile Val Tyr Ser Glu
305                 310                 315                 320 tat gac ccg tca agt cct ttc agt gaa gct tct gtg atg acg ctg ttg         1008
Tyr Asp Pro Ser Ser Pro Phe Ser Glu Ala Ser Val Met Thr Leu Leu
                325                 330                 335 acc aat ctt gct gac aga gaa ctg gtg cac atg atc acc tgg gcc aaa         1056
Thr Asn Leu Ala Asp Arg Glu Leu Val His Met Ile Thr Trp Ala Lys
            340                 345                 350 aga gtt cca ggg ttt gtg gat tta gca ctc cat gat cag gtc cat ctc         1104
Arg Val Pro Gly Phe Val Asp Leu Ala Leu His Asp Gln Val His Leu
        355                 360                 365 ctg gaa tgt gcc tgg tta gag ata ctg atg att ggc tta atc tgg cgt         1152
Leu Glu Cys Ala Trp Leu Glu Ile Leu Met Ile Gly Leu Ile Trp Arg
370                 375                 380 tca ttg gag cac cca gga aag ctt ttg ttt gct cct aac ctg tta ttg         1200
Ser Leu Glu His Pro Gly Lys Leu Leu Phe Ala Pro Asn Leu Leu Leu
385                 390                 395                 400 gac agg agt cag ggg atg tgt gtt gag ggt ttt gtg gag ata ttt gac         1248
Asp Arg Ser Gln Gly Met Cys Val Glu Gly Phe Val Glu Ile Phe Asp
                405                 410                 415 atg ctg ctg gcc act tct tct cgc ttt cga atg atg aat atc cag ggg         1296
Met Leu Leu Ala Thr Ser Ser Arg Phe Arg Met Met Asn Ile Gln Gly
            420                 425                 430 gaa gaa ttt gtt tgc ctt aaa tcc atc atc cta ctc aat tct ggt atc         1344
Glu Glu Phe Val Cys Leu Lys Ser Ile Ile Leu Leu Asn Ser Gly Ile
        435                 440                 445 tat aca ttt ctt tct agc acc cta aga tcg ctg gag gaa aaa gag cac         1392
Tyr Thr Phe Leu Ser Ser Thr Leu Arg Ser Leu Glu Glu Lys Glu His
        450                 455                 460 att cat cgt gtt cta gat aaa atc aca gac act ttg aca cat ttg atg         1440
Ile His Arg Val Leu Asp Lys Ile Thr Asp Thr Leu Thr His Leu Met
465                 470                 475                 480 gcc aaa tca ggc ctc tct ctg cag cag cag cat cga cga ttg gcc cag         1488
Ala Lys Ser Gly Leu Ser Leu Gln Gln Gln His Arg Arg Leu Ala Gln
                485                 490                 495 ctc ctc ctt atg ctt tcc cat atc aga cac atg agc aat aaa gga atg         1536
Leu Leu Leu Met Leu Ser His Ile Arg His Met Ser Asn Lys Gly Met
            500                 505                 510 gag cat ctc tac aac atg aaa tgc aag aat gtg gtc cct ctt tat gat         1584
Glu His Leu Tyr Asn Met Lys Cys Lys Asn Val Val Pro Leu Tyr Asp
        515                 520                 525 tta ctg ttg gaa atg cta gac gca cac cgg ctg cat gag aga cgc aca         1632
Leu Leu Leu Glu Met Leu Asp Ala His Arg Leu His Glu Arg Arg Thr
        530                 535                 540 ccc aca agt gaa cag gcc atg aac cag ctg aca aat gca tcc act tca         1680
Pro Thr Ser Glu Gln Ala Met Asn Gln Leu Thr Asn Ala Ser Thr Ser
545                 550                 555                 560 gtg cat tcc tta ccg cct tgc tac gtg aac aaa agg gaa gag gag aat         1728
Val His Ser Leu Pro Pro Cys Tyr Val Asn Lys Arg Glu Glu Glu Asn
                565                 570                 575
```

```
gag caa gaa gca gtg tga                                              1746
Glu Gln Glu Ala Val
        580

<210> SEQ ID NO 3
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 3
tcacactgct tcttgctcat tctcc                                            25

<210> SEQ ID NO 4
<211> LENGTH: 36
<212> TYPE: DNA
<213> ORGANISM: Artificial Sequence
<220> FEATURE:
<223> OTHER INFORMATION: Designed oligonucleotide primer for PCR

<400> SEQUENCE: 4
tatactagtt cacactgctt cttgctcatt ctcctc                                36

<210> SEQ ID NO 5
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 5
atgaccatga cccttcacac aaaaa                                            25

<210> SEQ ID NO 6
<211> LENGTH: 36
<212> TYPE: DNA
<213> ORGANISM: Artificial Sequence
<220> FEATURE:
<223> OTHER INFORMATION: Designed oligonucleotide primer for PCR

<400> SEQUENCE: 6
aaactagtac cagccaccat gaccatgacc cttcac                                36

<210> SEQ ID NO 7
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 7
ccatgccttt gttgctcatg tg                                               22

<210> SEQ ID NO 8
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 8
tctgggctca ctgaaatgta gactc                                            25

<210> SEQ ID NO 9
<211> LENGTH: 22
```

```
<212> TYPE: DNA
<213> ORGANISM: Artificial Sequence
<220> FEATURE:
<223> OTHER INFORMATION: Designed oligonucleotide primer for PCR

<400> SEQUENCE: 9
gggcacaacg actatatgtg tc                                              22

<210> SEQ ID NO 10
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 10
atgttccttg ctcactgcca ttagc                                           25

<210> SEQ ID NO 11
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 11
cagcgaggtt ggtcaacagc gtcatc                                          26

<210> SEQ ID NO 12
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 12
ccacctctgc ggtcttttcg                                                 20

<210> SEQ ID NO 13
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 13
aagagttcca gggtttgtgg                                                 20

<210> SEQ ID NO 14
<211> LENGTH: 25
<212> TYPE: DNA
<213> ORGANISM: Artificial Sequence
<220> FEATURE:
<223> OTHER INFORMATION: Designed oligonucleotide primer for reverse
                        transcription

<400> SEQUENCE: 14
tcaaattgct tcctgctcat ttccc                                           25

<210> SEQ ID NO 15
<211> LENGTH: 52
<212> TYPE: DNA
<213> ORGANISM: Artificial Sequence
<220> FEATURE:
<223> OTHER INFORMATION: Designed oligonucleotide to synthesize promoter
                        DNA
```

<400> SEQUENCE: 15
gatctcgact ataaagaggg caggctgtcc tctaagcgtc accacgactt ca        52

<210> SEQ ID NO 16
<211> LENGTH: 52
<212> TYPE: DNA
<213> ORGANISM: Artificial Sequence
<220> FEATURE:
<223> OTHER INFORMATION: Designed oligonucleotide to synthesize promoter
      DNA

<400> SEQUENCE: 16
agcttgaagt cgtggtgacg cttagaggac agcctgccct ctttatagtc ga        52

<210> SEQ ID NO 17
<211> LENGTH: 32
<212> TYPE: DNA
<213> ORGANISM: Artificial Sequence
<220> FEATURE:
<223> OTHER INFORMATION: Designed oligonucleotide primer for PCR

<400> SEQUENCE: 17
gccgaattca tgctgaaaca caagcgacaa ag                              32

<210> SEQ ID NO 18
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 18
gccgtcgact cacactgctt cttgctcatt ctc                             33

<210> SEQ ID NO 19
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 19
gccgaattcg agagagctga cgggcagagc aga                             33

<210> SEQ ID NO 20
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 20
gccagatctg ctcatagttg ctggcatacc act                             33

<210> SEQ ID NO 21
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 21
cctgctacca atcagtgcac                                            20

<210> SEQ ID NO 22

```
<211> LENGTH: 18
<212> TYPE: DNA
<213> ORGANISM: Artificial Sequence
<220> FEATURE:
<223> OTHER INFORMATION: Consensus sequence to be bound by Gal protein

<400> SEQUENCE: 22
cggacaactg ttgacccg                                                     18

<210> SEQ ID NO 23
<211> LENGTH: 20
<212> TYPE: DNA
<213> ORGANISM: Artificial Sequence
<220> FEATURE:
<223> OTHER INFORMATION: Consensus sequence to be bound by Lex protein

<400> SEQUENCE: 23
tactgtatgt acatacagta                                                   20

<210> SEQ ID NO 24
<211> LENGTH: 22
<212> TYPE: DNA
<213> ORGANISM: Artificial Sequence
<220> FEATURE:
<223> OTHER INFORMATION: Consensus sequence to be bound by Lac I
                        receptor protein

<400> SEQUENCE: 24
gaattgtgag cgcgcacaat tc                                                22

<210> SEQ ID NO 25
<211> LENGTH: 42
<212> TYPE: DNA
<213> ORGANISM: Artificial Sequence
<220> FEATURE:
<223> OTHER INFORMATION: Consensus sequence to be bound by Tetracyclin
                        receptor protein

<400> SEQUENCE: 25
tcgagtttac cactccctat cagtgataga gaaaagtgaa ag                          42

<210> SEQ ID NO 26
<211> LENGTH: 12
<212> TYPE: DNA
<213> ORGANISM: Artificial Sequence
<220> FEATURE:
<223> OTHER INFORMATION: Consensus sequence to be bound by ZFHD-1

<400> SEQUENCE: 26
taatgatggg cg                                                           12

<210> SEQ ID NO 27
<211> LENGTH: 13
<212> TYPE: DNA
<213> ORGANISM: Artificial Sequence
<220> FEATURE:
<223> OTHER INFORMATION: Consensus sequence to be bound by Estrogen
                        receptor
<220> FEATURE:
<221> NAME/KEY: variation
<222> LOCATION: 6
<223> OTHER INFORMATION: n=a or g or c or    t
<220> FEATURE:
<221> NAME/KEY: variation
<222> LOCATION: 7
<223> OTHER INFORMATION: n=a or g or c or t
<220> FEATURE:
<221> NAME/KEY: variation
<222> LOCATION: 8
```

```
<223> OTHER INFORMATION: n=a or g or c or t

<400> SEQUENCE: 27
ggtcannntg acc                                                          13
```